US 7,999,087 B2

(12) United States Patent
Dellinger et al.

(10) Patent No.: US 7,999,087 B2
(45) Date of Patent: Aug. 16, 2011

(54) 2'-SILYL CONTAINING THIOCARBONATE PROTECTING GROUPS FOR RNA SYNTHESIS

(75) Inventors: Douglas J. Dellinger, Boulder, CO (US); Agnieska Sierzchala, Boulder, CO (US); Marvin H. Caruthers, Boulder, CO (US); Geraldine F. Dellinger, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 806 days.

(21) Appl. No.: 11/985,598

(22) Filed: Nov. 15, 2007

(65) Prior Publication Data
US 2008/0227964 A1    Sep. 18, 2008

Related U.S. Application Data

(60) Provisional application No. 60/866,052, filed on Nov. 15, 2006, provisional application No. 60/928,782, filed on May 10, 2007.

(51) Int. Cl.
*C07H 19/00* (2006.01)
*C07H 21/00* (2006.01)
*C07H 21/02* (2006.01)

(52) U.S. Cl. .................... 536/22.1; 536/23.1; 536/25.3; 536/25.31

(58) Field of Classification Search .................. None
See application file for complete search history.

(56) References Cited

U.S. PATENT DOCUMENTS

| | | | |
|---|---|---|---|
| 5,889,136 A | 3/1999 | Scaringe et al. | |
| 6,111,086 A | 8/2000 | Scaringe | |
| 6,222,030 B1 | 4/2001 | Dellinger et al. | |
| 6,590,093 B1 | 7/2003 | Scaringe | |
| 6,630,581 B2 | 10/2003 | Dellinger et al. | |
| 7,101,986 B2 | 9/2006 | Dellinger et al. | |
| 7,759,471 B2 * | 7/2010 | Dellinger et al. | 536/22.1 |
| 2002/0058802 A1 | 5/2002 | Dellinger et al. | |
| 2004/0116687 A1 | 6/2004 | Dellinger et al. | |
| 2005/0048496 A1 | 3/2005 | Dellinger et al. | |
| 2005/0048497 A1 | 3/2005 | Dellinger et al. | |
| 2005/0048601 A1 | 3/2005 | Dellinger et al. | |
| 2005/0049407 A1 | 3/2005 | Dellinger et al. | |
| 2005/0049411 A1 | 3/2005 | Dellinger et al. | |
| 2006/0247430 A1 | 11/2006 | Dellinger et al. | |
| 2006/0293511 A1 | 12/2006 | Dellinger et al. | |
| 2007/0099859 A1 | 5/2007 | Dellinger et al. | |
| 2007/0100136 A1 | 5/2007 | Dellinger et al. | |
| 2007/0100137 A1 | 5/2007 | Dellinger et al. | |
| 2007/0100138 A1 | 5/2007 | Dellinger et al. | |

* cited by examiner

*Primary Examiner* — Traviss C McIntosh, III

(57) ABSTRACT

Nucleoside monomers, nucleic acids, e.g., oligonucleotides and polynucleotides, methods of making each, methods of deprotecting each, and the like are disclosed herein. Aspects of the invention include 2' silyl containing thiocarbonate protecting groups. Corresponding compositions and methods are provided.

22 Claims, 4 Drawing Sheets

0.7M ZnBr$_2$ in CHCl$_3$/MeOH (9:1) RT, 1 hour 0.7M ZnBr$_2$ in CHCl$_3$/MeOH (9:1) RT, 6 hours 1M ZnBr$_2$ in CHCl$_3$/MeOH (1:4) RT, 1 hour .1M ZnBr$_2$ in CHCl$_3$/MeOH (1:4) RT, 6 hours

2'-SILYL CONTAINING THIOCARBONATE PROTECTING GROUPS FOR RNA SYNTHESIS

CROSS REFERENCE TO RELATED APPLICATIONS

This application claims the benefit under 35 U.S.C. §119(e) of prior U.S. provisional application Ser. No. 60/866,052 filed Nov. 15, 2006, and Ser. No. 60/928,782 filed May 10, 2007, the disclosures of which applications are herein incorporated by reference.

INTRODUCTION

Chemical synthesis of RNA is a much more difficult task than chemical synthesis of DNA, because the 2'-hydroxyl group in the ribose has to be protected during chemical synthesis. The close proximity of a protected 2'-hydroxyl to the internucleotide phosphate presents problems, both in terms of formation of the internucleotide linkage and in the removal of the 2'-protecting group once the oligoribonucleotide is synthesized. In addition, the internucleotide bond in RNA is far less stable than that in DNA.

Until recently, the typical approach to RNA synthesis utilized ribonucleoside monomers in which the 5'-hydroxyl group was protected by the acid-labile dimethoxytrityl (DMT) protecting group, which can be removed under acidic conditions after coupling of the monomer to the growing oligoribonucleotide. Various acid-stable protecting groups have been placed on the 2'-hydroxyl to prevent isomerization and cleavage of the internucleotide bond during the acid deprotection step. The most popular of these acid-stable protecting groups seems to be the tert-butyl-dimethylsilyl group, known as TBDMS (Ogilvie et al., Can. J. Chem. 57: 2230-2238 (1979)). The use of TBDMS as 2'-protecting group dominated the previously small market for RNA chemical synthesis for a very long time (Usman et al., J. Am. Chem. Soc. 109: 7845 (1987); Ogilvie et al., Proc. Natl. Acad. Sci. USA 85: 5764 (1988)).

However, oligoribonucleotide syntheses carried out using TBDMS are by no means satisfactory and typically produce RNA products of poor quality. For example, several publications have reported the migration of the alkylsilyl group under a variety of conditions (Scaringe et al., Nucleic Acids Research 18(18): 5433-5441 (1990); Hogrefe et al., Nucleic Acids Research 21(20): 4739-4741 (1993)). As a result, the TBDMS protecting group migrates from the 2'-position to the 3'-position. Furthermore, during the synthesis of the monomer (e.g., 5'-O-DMT-2'-O-TBDMS-ribo-3'-O-(beta-cyanoethyl, N-diisopropyl)phosphoramidite), introduction of the 2'-silyl group is non-regioselective, thus it can be added to either the 2' or 3' position. Combined with the added chemical requirements to prevent migration of the silyl group during phosphoramidite production, synthesis of the monomer is challenging and costly. It is also well known in the art that the coupling efficiency of these monomers is greatly decreased due to steric hindrance of the 2'-TBDMS protecting group, which not only affects the yield and purity of the full-length product, but also limits the length of the oligoribonucleotide that can be achieved by this method.

Alternatively, many researchers have pursued the use of acid-labile groups for the protection of the 2'-hydroxyl moiety. The classic acid-labile protecting group is the 2'-acetal moiety, which was initially developed by Reese (reviewed by Reese C B, Org. Biomol. Chem. 3(21): 3851-68 (2005)), such as tetrahydropyran (THP) or 4-methoxy-tetrahydropyran (MTHP), 1-(2-chloroethoxy)ethyl (CEE) (Sakatsume et al., Tetrahedron 47: 8717-8728 (1991), and 1-(2-fluorophenyl)-4-methoxypiperidin-4-yl (FPMP) (Rao et al., J. Chem. Soc., Perkin Trans. 2:43-55 (1993); Capaldi et al., Nucleic Acids Research 22(12):2209-2216 (1994)).

One of the advantages of acetal protecting groups compared with silyl ether protecting groups is that they can be introduced regioselectively into the 2' position through the use of the Markiewicz protecting group: tetraisopropyldisiloxane-1,3-diyl. This protecting group, also known as TIPS, simultaneously blocks the 5'- and 3'-hydroxyls to allow complete regioselectivity upon introduction of the acetal group on to the 2'-hydroxyl (Markiewicz W T, J. Chem Research (S) 24-25 (1979)). Another advantage is that the phosphoramidite coupling with 2'-acetal protected monomers is typically more efficient than with trialkyl silanes. The problems encountered when using the combination of 5'-O-DMT and 2'-O-acetals groups reside in the difficulty to find suitable 2'-O acetal groups that are both completely stable to the anhydrous acidic conditions used to remove the 5'O-DMT group and completely labile to the mild aqueous acid conditions used to remove this 2'-acetal protecting group, while not cleaving the internucleotide bond of the RNA. The removal of acetals that are stable under DMT deprotection conditions typically requires prolonged exposure to acidic conditions that degrade the RNA. To inhibit the loss of the 2'-protecting group, the 5'-9-phenylxanthen-9-yl (Pix) group was applied, which is more labile than the DMT protecting group.

Even considering all of these innovations, the inability to find a viable combination of 2'-acetal and 5'-acid labile protecting groups that fits into the standard phosphoramidite synthesis cycle has prevented effective commercialization of these chemical schemes. Conversely, acetals used in combination with 5' protecting groups such as leuvinyl and 9-fluorenylmethyloxycarbonyl (FMOC) that are deprotected under non-acidic conditions like hydrazinolysis have not met significant success.

Scaringe et al. developed a set of 5- and 2-protecting groups that overcome the problems associated with use of 5'-DMT. This method uses a 5'-silyloxy protecting group (U.S. Pat. Nos. 5,889,136; 6,111,086; and 6,590,093), which require silicon-specific fluoride ion nucleophiles to be removed, in conjugation with the use of optimized 2'-orthoesters protecting groups (ACE). Although the coupling efficiency is greatly increased and the final deprotection facile under pH conditions at which RNA is stable, the use of fluoride anions to deprotect the 5'-protecting groups prior to each condensation cycle is troublesome. Moreover, this chemistry requires atypical nucleoside protecting groups and custom synthesized monomers, so it cannot utilize many commercially available standard monomers.

The demand for synthetic RNA has been increasing, largely due to the discovery of RNA interference. Therefore, it is desirable to develop improved RNA synthesis schemes, particularly 2'-protecting groups, to meet the growing needs.

SUMMARY

Aspects of the invention include 2'-hydroxyl protecting groups (i.e., 2'HPG groups), where the 2'-hydroxyl protecting groups are silyl containing thiocarbonate protecting groups. While still containing a silyl group, these new protecting groups can be introduced selectively in a high yielding reaction, and not be subject to isomerization during introduction or deprotection. It has also been found that these protecting groups allow a very efficient coupling reaction when synthesizing RNA.

DEFINITIONS

Figure 1:
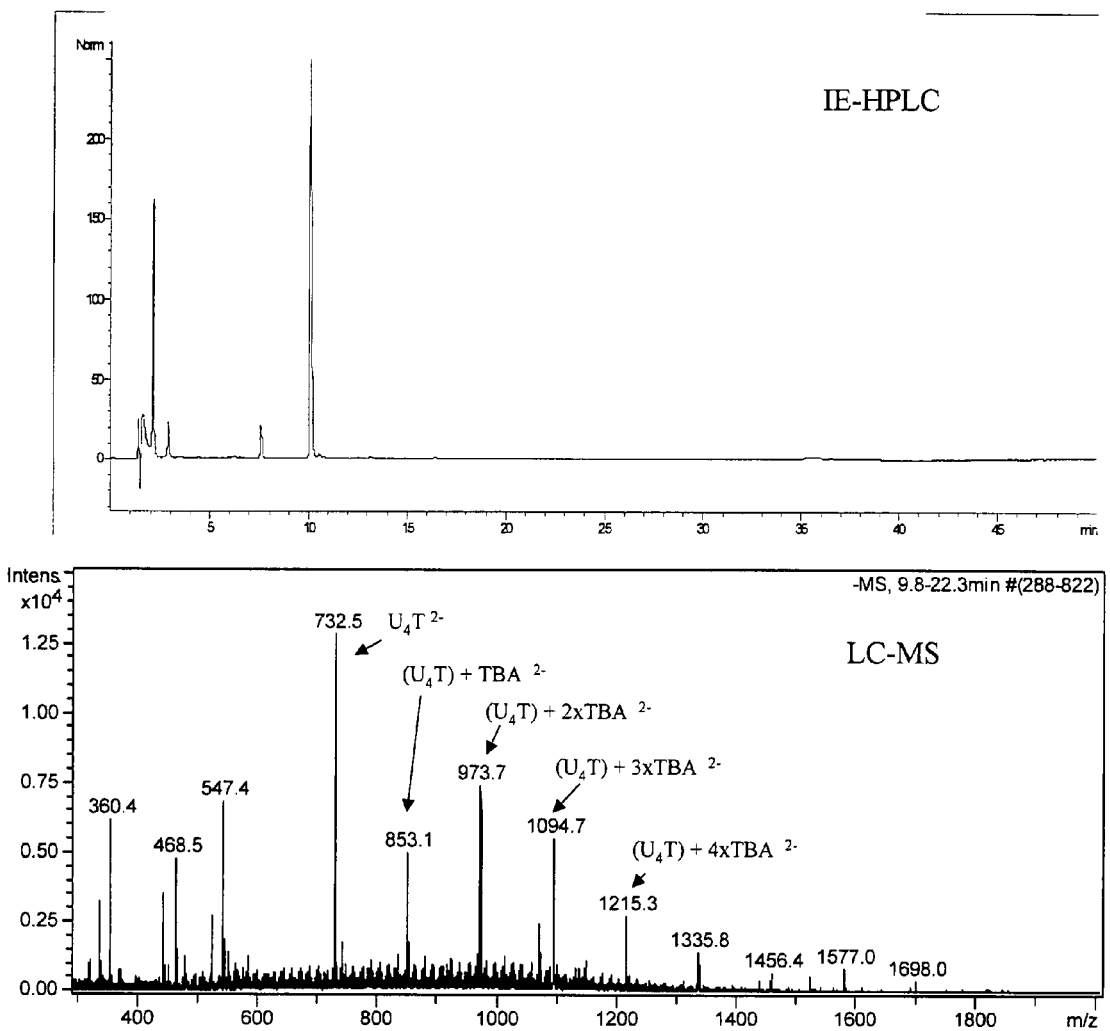
FIGS. 1 to 4 provide results of IE-HPLC and LC-MS runs as described in the Experimental section, below.

Prior to describing the invention in further detail, the terms used in this application are defined as follows unless otherwise indicated.

A "nucleotide" or a "nucleotide moiety" refers to a subunit of a nucleic acid (whether DNA or RNA) which may include, but is not limited to, a phosphate group, a sugar group and a nitrogen containing base. Other groups (e.g., protecting groups) can be attached to any component(s) of a nucleotide or nucleotide moiety.

A "nucleoside" or a "nucleoside moiety" refers to a nucleic acid subunit including a sugar group and a nitrogen containing base. Other groups (e.g., protecting groups) can be attached to either or both components of a nucleoside or nucleoside moiety.

An "oligonucleotide" generally refers to a nucleotide multimer of 2 to 300 nucleotides in length, while a "polynucleotide" generally refers to a nucleotide multimer having 100 or more nucleotides. The terms "oligonucleotide" and "polynucleotide" are often used interchangeably, consistent with the context of the sentence and paragraph in which they are used in.

The term "nitrogen-containing base" includes not only the naturally occurring purine and pyrimidine bases, e.g., adenine (A), thymine (T), cytosine (C), guanine (G), or uracil (U), but also modified purine and pyrimidine bases and other heterocyclic bases which have been modified. Such bases include, e.g., diaminopurine, inosine, 3-nitropyrrole, 5-nitroindole, alkylated purines or pyrimidines, acylated purines or pyrimidines, thiolated purines or pyrimidines, and the like, or bases with the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing. Analogs of interest include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, 2-deoxyinosine, 1-methylinosine, hypoxanthine, xanthine, 2-aminopurine, 6-hydroxyaminopurine, 6-thiopurine, and 2,6-diaminopurine.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

A "group" includes both substituted and unsubstituted forms. Substituents of interest include one or more lower alkyl, amino, imino, amido, alkylamino, arylamino, alkoxy, aryloxy, thio, alkylthio, arylthio, or aryl, or alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are chosen so as not to substantially adversely affect reaction yield (for example, not lower it by more than 20% (or 10%, or 5%, or 1%) of the yield otherwise obtained without a particular substituent or substituent combination). Further, substituents are chosen so as to be chemically compatible with the other groups present and to avoid side reactions known to those skilled in the art. For example, an alcohol would not be substituted with a lithium group, as the hydroxide of the alcohol and the lithium group are incompatible and would react with each other. For any group in this disclosure, each substituent may include up to 40, 35, 30, 25, 20, 18, 16, 14, 12, 11, 10, 9, 8, 7, 6, 5, 4 or 3 carbon atoms. Overall, the total number of carbon atoms in all the substituents for any group is, in certain embodiments, 80, 75, 70, 65, 60, 55, 50, 45, 40, 35, 30, 25, 20, 18, 16, 14, 12, 11, 10, 9, 8, 7, 6, 5, 4 or 3 or less.

A "phospho" group includes a phosphodiester, phosphotriester, and H-phosphonate groups. In the case of either a phospho or phosphite group, a chemical moiety other than a substituted 5-membered furyl ring may be attached to 0 of the phospho or phosphite group which links between the furyl ring and the P atom.

A "protecting group" is used in the conventional chemical sense as a group, which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "O-protecting group" refers to a protecting group where the protected group is a hydroxyl. A "terminal reactive-site hydroxyl" is the terminal 5'-hydroxyl during 3'-5' polynucleotide synthesis, or the 3'-hydroxyl during 5'-3' polynucleotide synthesis. An "acid-labile protected hydroxyl" is a hydroxyl group protected by a protecting group that can be removed by acidic conditions. Similarly, an "alkaline-labile protecting group" is a protecting group that can be removed by alkaline conditions.

The term "phosphoramidite group" is employed in its conventional sense to refer to a group comprising the structure —P—(OR$^{12}$)(NR$^{13}$R$^{14}$), wherein each of R$^{12}$, R$^{13}$, and R$^{14}$ is independently a hydrocarbyl, substituted hydrocarbyl, heterocycle, substituted heterocycle, aryl or substituted aryl. R$^{12}$, R$^{13}$, and R$^{14}$ may be selected from lower alkyls, lower aryls, and substituted lower alkyls and lower aryls (e.g., substituted with structures containing up to 18, 16, 14, 12, 11, 10, 9, 8, 7, 6, 5, 4, 3 or 2 carbons). In some embodiments, $R^{12}$ is 2-cyanoethyl or methyl, and either or both of $R^{13}$ and $R^{14}$ is isopropyl. $R^{13}$ and $R^{14}$ can optionally be cyclically connected. $R^{12}$ may optionally be a BEST or BESC protecting group as described herein.

The term "alkyl" refers to a saturated straight chain, branched, or cyclic hydrocarbon group of 1 to 30 carbon atoms. Alkyls of interest contain 1-24, 1-20, 1-16, 1-12, 1-10, 1-8, 1-6 or 1-4 carbon atoms. A "lower alkyl" is an alkyl with 1 to 6 carbon atoms. Exemplary alkyls include methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. Lower alkyls include methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl. Cycloalkyls may have from 3 to 10 carbon atoms in their ring structure, such as 5, 6 or 7 carbons in the ring structure.

The term "alkenyl" refers to a branched, unbranched, or cyclic hydrocarbon group of 2 to 30 carbon atoms containing at least one double bond, such as ethenyl, vinyl, allyl, octenyl, decenyl, and the like. An alkenyl may contain 2-24, 2-20, 2-16, 2-12, 2-10, 2-8, 2-6 or 2-4 carbon atoms. The term "lower alkenyl" refers to an alkenyl group of two to six carbon atoms, and specifically includes vinyl and allyl. The term "cycloalkenyl" refers to cyclic alkenyl groups.

The term "alkynyl" refers to a branched or unbranched hydrocarbon group of 2 to 30 carbon atoms containing at least one triple bond, such as acetylenyl, ethynyl, n-propynyl, isopropynyl, n-butynyl, isobutynyl, t-butynyl, octynyl, decynyl and the like. An alkynyl may contain 2-24, 2-20, 2-16, 2-12, 2-10, 2-8, 2-6 or 2-4 carbon atoms. The term "lower alkynyl" refers to an alkynyl group of two to six carbon atoms, and includes, for example, acetylenyl and propynyl. The term "cycloalkynyl" refers to cyclic alkynyl groups.

The term "hydrocarbyl" refers to alkyl, alkenyl or alkynyl.

The term "substituted hydrocarbyl" refers to hydrocarbyl moieties having substituents replacing a hydrogen on one or more carbons of the hydrocarbon backbone of the hydrocarbyl backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. Moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like. Further, substituents are chosen so as to be chemically compatible with the other groups present and to avoid side reactions known to those skilled in the art. For example, a hydroxide bearing hydrocarbyl would not be substituted with a lithium group, as the hydroxide and the lithium groups are incompatible and would react with each other.

The term "alkoxy" means an alkyl group linked to oxygen and may be represented by the formula: R—O—, wherein R represents the alkyl group. An example is the methoxy group $CH_3O—$.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like. Further, substituents are chosen so as to be chemically compatible with the other groups present and to avoid side reactions known to those skilled in the art. For example, a hydroxide bearing aryl group would not be substituted with a lithium group, as the hydroxide and the lithium groups are incompatible and would react with each other.

The terms "halogen" and "halo" refer to fluorine, chlorine, bromine, or iodine.

The term "heterocycle", "heterocyclic", "heterocyclic group" or "heterocyclo" refers to fully saturated or partially or completely unsaturated cyclic groups having at least one heteroatom in at least one carbon atom-containing ring, including aromatic ("heteroaryl") or nonaromatic (for example, 3 to 13 member monocyclic, 7 to 17 member bicyclic, or 10 to 20 member tricyclic ring systems). Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions. Nitrogen-containing bases are examples of heterocycles. Other examples include piperidinyl, morpholinyl and pyrrolidinyl.

The terms "substituted heterocycle", "substituted heterocyclic", "substituted heterocyclic group" and "substituted heterocyclo" refer to heterocycle, heterocyclic, and heterocyclo groups substituted with one or more groups e.g., selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring. Further, substituents are chosen so as to be chemically compatible with the other groups present and to avoid side reactions known to those skilled in the art. For example, a hydroxide bearing heterocycle would not be substituted with an acyl halide, as the hydroxide and the acyl halide groups are incompatible and would react with each other.

When used herein, the terms "hemiacetal", "thiohemiacetal", "acetal", and "thioacetal", refer to a chemical moiety in which a single carbon atom is geminally disubstituted with either two oxygen atoms or a combination of an oxygen atom and a sulfur atom. In addition, when using the terms, it is understood that the carbon atom may actually be geminally disubstituted by two carbon atoms, forming ketal, rather than acetal, compounds.

The term "electron-withdrawing group" is employed in its art-recognized to refer to the tendency of a substituent to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry 251-59, McGraw Hill Book Company, New York, (1977). Exemplary electron-withdrawing groups include nitro, acyl, formyl, sulfonyl, trifluoromethyl, cyano, chloride, and the like.

The term "electron-donating group" is employed in its art recognized sense to refer to the tendency of a substituent to repel valence electrons from neighboring atoms (i.e., the substituent is less electronegative with respect to neighboring atoms). Exemplary electron-donating groups include amino, methoxy, alkyl (including C1-6 alkyl that can have a linear or branched structure), C4-9 cycloalkyl, and the like.

The term "deprotecting simultaneously" refers to a process which aims at removing different protecting groups in the same process and is performed substantially concurrently or concurrently. However, as used herein, this term does not imply that the deprotection of the different protecting groups occur at exactly the same time or with the same rate or same kinetics.

The term "carbohydrate" can refer, without being limited, to a sugar, a disaccharide, an oligosaccharide, or a polysaccharide, including substituted forms thereof.

Hyphens, or dashes are used at various points throughout this specification to indicate attachment, e.g. where two named groups are immediately adjacent to a dash in the text, this indicates that the two named groups area attached to each other. Similarly, a series of named groups with dashes between each of the named groups in the text indicated the named groups are attached to each other in the order shown. Also, a single named group adjacent a dash in the text indicates that the named group is typically attached to some other, unnamed group. In some embodiments, the attachment indicated by a dash may be, e.g., a covalent bond between the adjacent named groups. At various points throughout the specification, a group may be set forth in the text with or without an adjacent dash, (e.g. amido or amido-, further e.g. alkyl or alkyl-, yet further Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

Dashed lines (e.g., ------) are used throughout the specification adjacent to named groups to indicate attachment to some other, unnamed group.

DETAILED DESCRIPTION

As summarized above, aspects of the invention include 2'-hydroxyl protecting groups (i.e., 2'HPG groups), where the 2'-hydroxyl protecting groups are silyl containing thiocarbonate protecting groups. While still containing a silyl group, these new protecting groups can be introduced selectively in a high yielding reaction, and not be subject to isomerization during introduction or deprotection. It has also been found that these protecting groups allow a very efficient coupling reaction when synthesizing RNA.

Aspects of the invention further include nucleoside monomers that include the protecting groups of the invention, as well as methods of synthesizing nucleic acids using the protecting groups of the invention. In addition, kits that include reagents for practicing the methods are provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be noted that, as is conventional in drawing some chemical structures, some of the hydrido groups are omitted from the drawn structures for clarity purposes, but should be understood to be present, e.g. where necessary to completely fill out the valence bonding of a carbon in a drawn structure.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, protecting groups of the invention will first be reviewed in greater detail, primarily in view of 2' protected nucleoside embodiments thereof. Next, methods of using protected monomers of the invention, primarily in terms of nucleic acid synthesis, are provided. Following these sections, a review of different applications in which the methods and products of the invention find use is provided. Finally, kits finding use in practicing various embodiments of the invention are described in greater detail.

Silyl Containing Thiocarbonate Protecting Groups and Monomers Protected by the Same As summarized above, aspects of the invention include silyl containing thiocarbonate protecting groups and monomers that include the same. In general, silyl containing thiocarbonate protecting groups can be used as protecting groups for a variety of different types of monomers. However, for ease of description the following discussion focuses primarily on use of the protecting groups of the invention in the context of protection of 2' hydroxyl moieties of nucleoside monomers.

Aspects of the invention include nucleoside monomers that include one or more silyl containing thiocarbonate protecting groups. These groups may be employed as hydroxyl protecting groups, such as 2' hydroxyl protecting groups.

2' protecting nucleoside monomers according to embodiments of the invention are described by the structure of Formula (I):

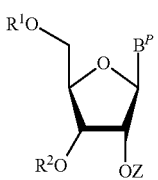

I wherein:

B$^P$ is a protected or unprotected nitrogen-containing base;

R$^1$ and R$^2$ are each independently H, a phosphoroamidate group, a hydroxyl protecting group, or R$^1$ and R$^2$ are linked to form a 1,3-tetraisopropyldisiloxane (TIPS) group; and Z is a silyl containing thiocarbonate protecting group.

The heterocyclic base may be a conventional purine or pyrimidine base, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, or the like. The purine or pyrimidine base may also be an analog of the foregoing. Suitable analogs include, but are not limited to: 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In certain embodiments, the group Z has the structure of formula (II):

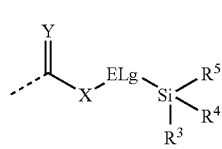

II wherein:

the dashed line indicates the site of attachment to the rest of the molecule (e.g., to the 2' oxygen of the protected nucleoside monomer);

X and Y are each independently a sulfur or oxygen atom, wherein in any given embodiments one of X and Y is sulfur and the other of X and Y is oxygen, so that the group is a thiocarbonate group;

R$^3$, R$^4$, and R$^5$ are each independently selected from hydrocarbyls, substituted hydrocarbyls, aryls, and substituted aryls, where in certain embodiments, R$_3$, R$_4$, and R$_5$, if substituted, are not linked to the silicon atom via an oxygen atom;

ELg is selected from the group consisting of an ethylene group, a substituted ethylene group, —(CH$_2$CH$_2$O)$_n$—CH$_2$CH$_2$—, substituted —(CH$_2$CH$_2$O)$_n$—CH$_2$CH$_2$—, the following functional groups, and any repeats and combinations of the following functional groups:

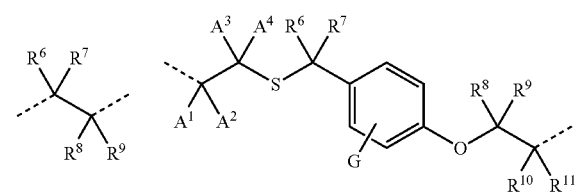

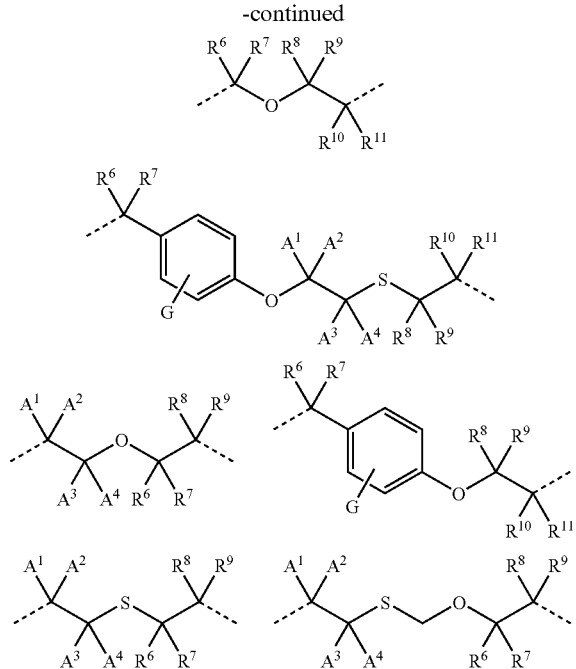

wherein:

each of $R^6$, $R^7$, $R^8$, $R^9$, $R^{10}$, and $R^{11}$, when present, is independently selected from the group consisting of H, hydrocarbyls, substituted hydrocarbyls, aryls, and substituted aryls;

each of $A^1$, $A^2$, $A^3$, and $A^4$ is independently an allowable substituent for episulfide formation;

G is one or multiple substituents on the phenyl ring independently selected from the group consisting of H, hydrocarbyls, substituted hydrocarbyls, aryls, and substituted aryls; and n is an integer from 1 to 8.

In certain embodiments, $R^1$ is a dimethoxytrityl (DMT) group. In certain embodiments, $R^2$ is a phosphoramidite group. In certain embodiments, BP is protected by a BES protecting group, such as a BEST or BESC protecting group.

In certain embodiments, Z is a protecting groups, such that the nucleoside monomers have the structure shown in Formula (IIIa) or Formula (IIIb):

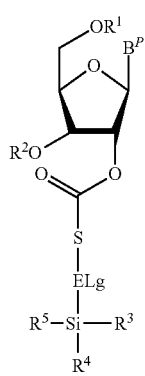

IIIa

IIIb

Specific examples of silyl containing thiocarbonate protecting groups in accordance with the invention include the following thiocarbonates, i.e., compounds of Formula II wherein X=S and Y=O (also illustrated by Formula IIIa):

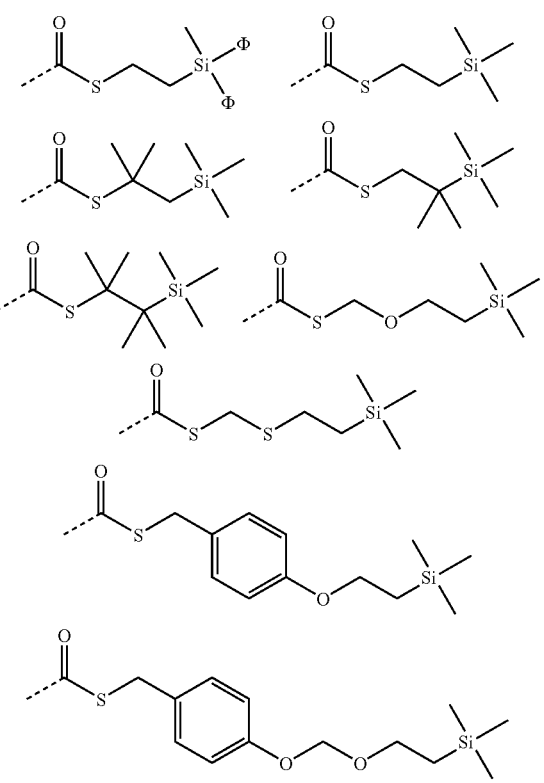

Further examples of the silyl containing thiocarbonate protecting groups in accordance with embodiments of the invention include the following thiocarbonyl carbonates, i.e., compounds of Formula II wherein X=O and Y=S (also illustrated by Formula IIIb):

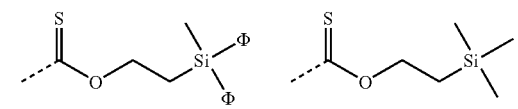

-continued

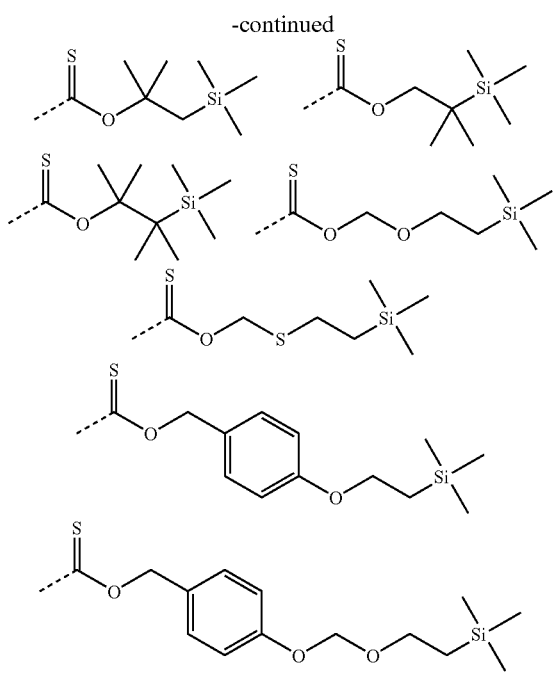

The protecting group containing nucleoside monomers can be produced using any convenient protocol. In certain embodiments, protected nucleoside monomers of the invention are produced using a protocol in which a nucleoside monomer having the structure shown in Formula (IV)

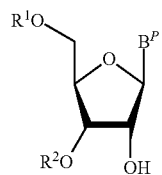

IV wherein:
BP is a protected or unprotected nitrogen-containing base; and
$R^1$ and $R^2$ are each independently H, a phosphoroamidate group, a hydroxyl protecting group, or $R^1$ and $R^2$ are linked to form a 1,3-tetraisopropyldisiloxane (TIPS) group;
is contacted with a compound having the structure: Z-LG, wherein:
Z is a beta-eliminating silyl protecting group; and
LG is a leaving group, such as a halo group;
under conditions sufficient to produce a 2 protected nucleoside monomer of the structure of Formula (I).

I

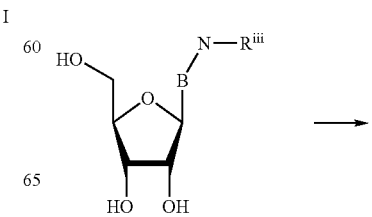

LG may be any convenient leaving group. The ability to introduce the protecting group using an activated carbonate, thiocarbonate, dithiocarbonate, or thiocarbonyl carbonate, such as dithiochloroformate, in general leads to high yield synthesis of the 2'-hydroxyl protected monomers. Leaving or activating groups include, but are not limited to: chloro, p-nitrophenoxy, pentafluoro phenoxy, O-succinimidyl, trichloromethyl, bromo, and iodo.

In further embodiments of nucleoside monomer synthesis methods, Z has the structure of Formula (II), with the same limitations on Formula (II) as described above.

II

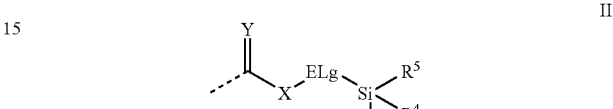

In additional embodiments of nucleoside monomer synthesis, Z has the structure of Formula (Va), Formula (Vb).

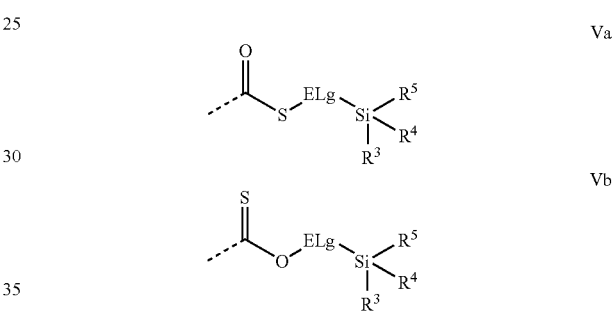

In certain embodiments of nucleoside monomer synthesis methods, $R^1$ and $R^2$ are linked to form a 1,3-tetraisopropyldisiloxane (TIPS) group. Such methods may further include a step of removing said TIPS group, e.g., by contacting with a suitable nucleophile, such as fluoride ions. This embodiment is described in greater detail below.

With the compounds of the present invention, specific reaction at the 2'-hydroxyl (regioselectivity) can be achieved by the transient protection of the 5' and 3'-hydroxyl groups through the use of a Markewicz protecting group. For example, 1,3-tetraisopropyl disiloxane (TIPS) is a transient blocking group that can be used to block the 5' and 3' hydroxyls simultaneously, thereby allowing the 2'-hydroxyl to react regioselectively. The 1,3-tetraisopropyl disiloxane group is subsequently removed using a solution of fluoride ions. Thus, the compounds of the present invention can be prepared easily and cost-effectively. In the exemplary illustration below, $R^i$ is a silyl containing thiocarbonate hydroxyl protecting group, and $R^{iii}$ is a protecting group for the nitrogen-containing base.

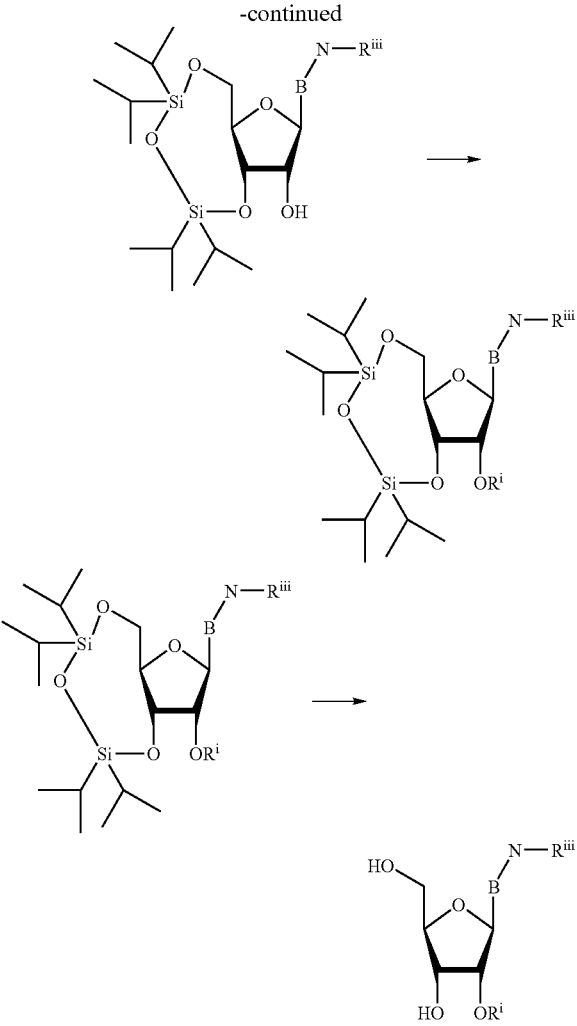

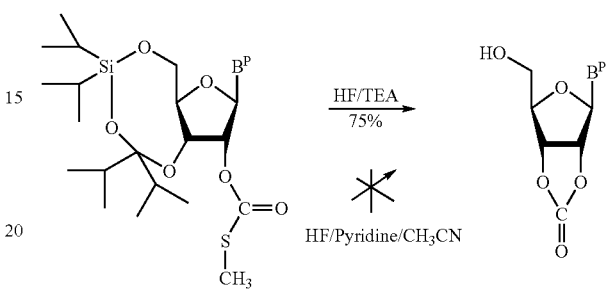

Because the required deprotection conditions of the TIPS group uses fluoride anions, 2'-protecting groups that contain silyl or silicon atoms, e.g., such as protecting groups of the invention, had been thought to be incompatible with this regioselective approach (Beigelman L, and Serebryany V, Nucleosides, Nucleotides, and Nucleic Acids 22: 1007-1009 (2003)). However, it has been shown that with the protected 2'-hydroxyl compounds described herein, and the conditions developed to deprotect the TIPS group, this regioselective transient protection can be performed with unprecedented efficiency. Specific compositions and methods have been developed to deprotect selectively the TIPS protection while preserving the 2'-protecting group. For example, the use of HF/pyridine allows selective deprotection of the TIPS while the thiocarbonate, dithiocarbonate or thiocarbonyl carbonate protecting group is preserved.

During or after the selective removal of the TIPS protecting group, it is important to consider the possible further reaction of the free 3'-hydroxyl to form a cyclic carbonate. Thiocarbonates, dithiocarbonates and thiocarbonyl carbonates on the 2'position do not undergo cyclization during TIPS removal with controlled conditions of HF/pyridine/CH$_3$CN. On the other hand, thiocarbonates, dithiocarbonates, or thiocarbonyl carbonates cyclize to a much greater extent when HF/TEA is used instead of HF/Pyridine/CH$_3$CN (see scheme below). This cyclization, while undesirable, produces a cyclic carbonate that can be readily separated from the desired product. In these deprotecting reactions employing HF, complexes of HF, such as HF-TEMED or HF-TMA, can also be used. Other solvents, e.g., dioxane, THF, or methylene chloride, can also be used, although under certain conditions such solvents may result in partial loss of the thiocarbonate, dithiocarbonate or thiocarbonyl carbonate group owing to the formation of a cyclic carbonate. Again, the cyclic carbonate is readily separable from the desired product.

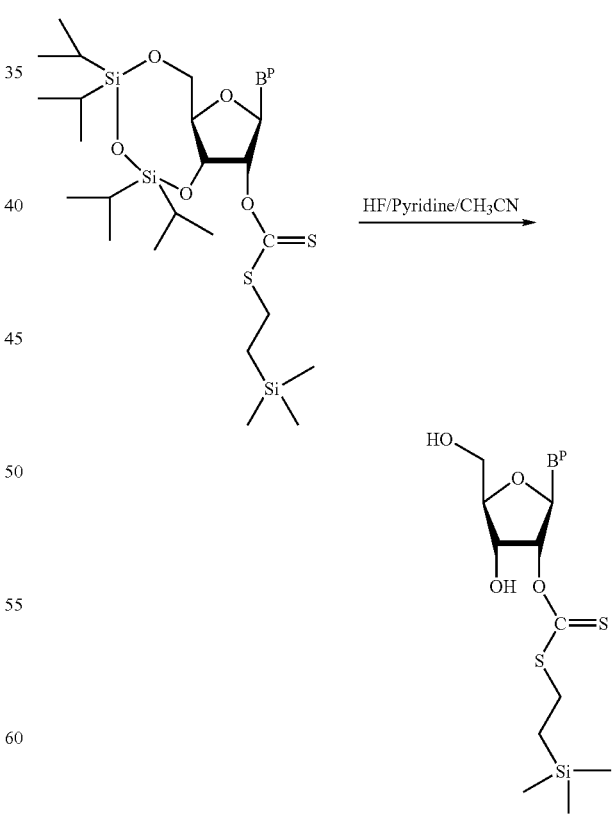

Selective removal of the silyl ether containing TIPS in the presence of a silylethyl functionality, in conjunction with the thiocarbonate, dithiocarbonate or thiocarbonyl carbonate functionality of the silyl containing thiocarbonate protecting group, enables the deprotection of the 5' and 3' hydroxyl without removal of the 2'protecting group, and without formation of the cyclic carbonate.

Activated carbonates, thiocarbonates, dithiocarbonates or thiocarbonyl carbonates, such as dithiochloroformates, are also reactive with, and provide stable protection of, the exocyclic amine groups of the heterobases. Thus, in certain embodiments, the thiocarbonate protecting groups are used to protect the nitrogen-containing base, allowing for the simultaneous protection of the 2'-hydroxyl and exocyclic amine. Synthesis of the RNA phosphoramidites therefore becomes very straightforward and easy, as well as very cost-efficient. As exemplified in the synthesis scheme below, this can be accomplished using 1,1,3,3-tetraisoprypyldisiloxane protected nucleosides (the Markeiwicz protecting group). This simultaneous protection strategy reduces significantly the number of steps and complexity of making RNA monomers. Coupled with the high reaction yield of chloroformates, thiochloroformates, dithiochloroformates, and thiocarbonyl chloroformates, this strategy reduces the cost of RNA precursor monomers to a similar level as that of DNA precursor monomers in certain embodiments.

one-step final deprotection of the RNA, with the bases and the 2'-hydroxyl groups being deprotected concurrently.

In some other embodiments of the present invention, the nitrogen-containing bases are protected by blocking groups other than thiocarbonates. These kinds of nucleoside monomers can be synthesized by starting from a nucleoside in which the nitrogen-containing base is already protected, for example by an acetyl, difluoroacetyl, trifluoroacetyl, isobutyryl, benzoyl, 9-fluorenylmethoxycarbonyl, phenoxyacetyl, dimethylformamidine, or N,N-diphenyl carbamate. The nucleoside can then be reacted with TIPSCl$_2$ and chloroformate, thiochloroformate, dithiochloroformate or thiocarbonyl chloroformate, proceeding as described in the scheme above. See also protecting groups disclosed in U.S. provisional application Ser. No. 60/866,052 and Ser. No. 60/928,

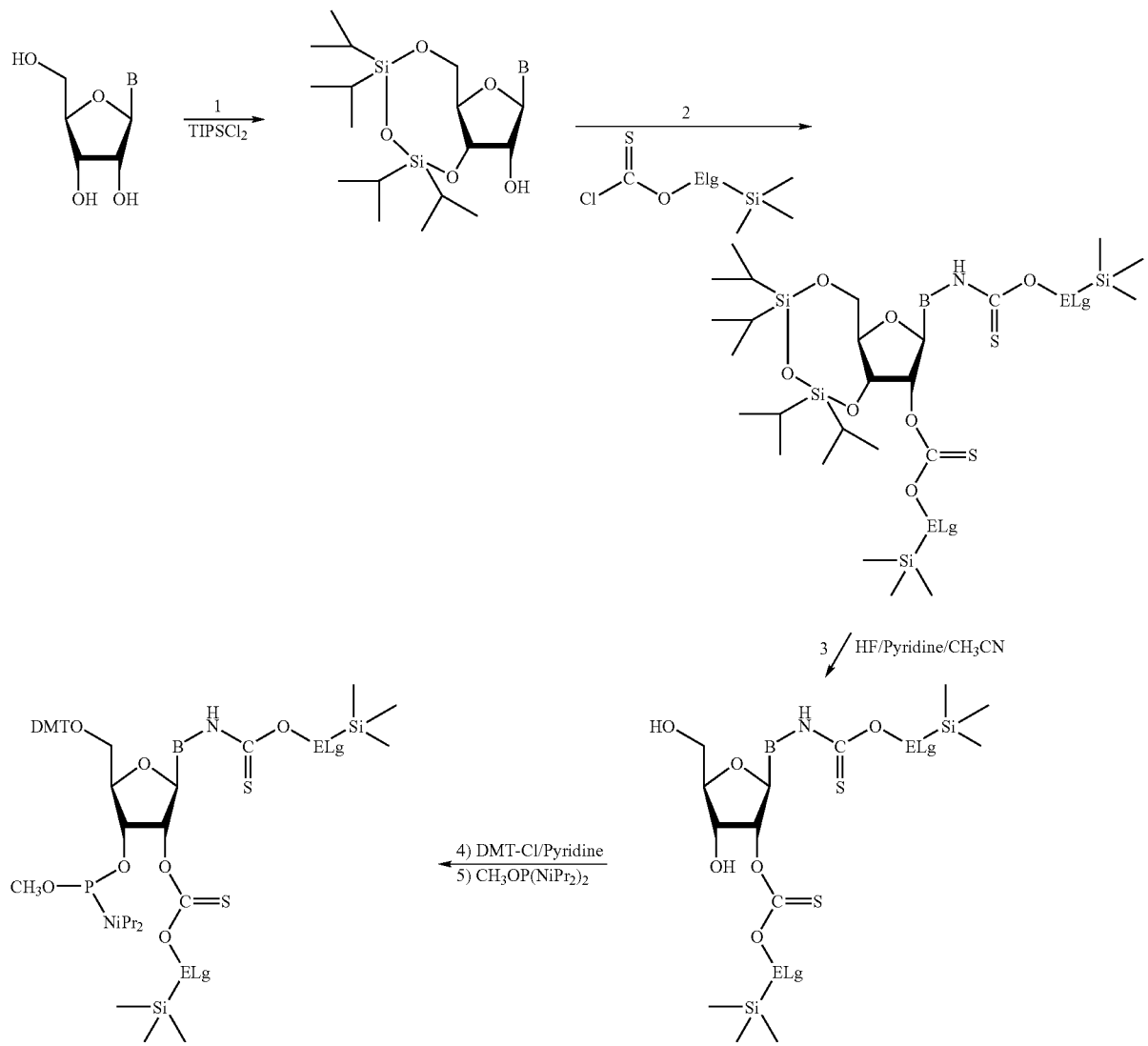

Exemplary Synthesis Scheme for Best RNA Monomers

The protection of the nitrogen-containing base with a silyl containing thiocarbonate protecting groups also allows for 782, the disclosures of the protecting groups of these applications being incorporated herein by reference.

Polymeric Synthesis Using Silyl Containing Thiocarbonate-Protected Monomers

Protected monomers of the invention find use in the synthesis of a variety of different types of polymers, including nucleic acids. In certain embodiments, the protected monomers of the invention are employed in synthesis of ribonucleic acids, e.g., solid phase or solution phase synthesis of ribonucleic acids. Synthesis in accordance with the invention can be performed in either direction: from 3' to 5' or from 5' to 3'. For example, in the 3' to 5' direction, a first nucleoside monomer with a 5'-OH and a 3'-protecting group is coupled with a second nucleoside monomer having a 3'-phosphoramidite and a 5'-protecting group. The first nucleoside monomer is optionally bound to a solid support, e.g., where synthesis is carried out using solid phase synthesis protocols. Alternatively, the synthesis can be performed in solution.

After the coupling step, in which the 5'-OH and the 3'-phosphoramidite condense to form a phosphite triester linkage and result in a dinucleotide, the dinucleotide is capped/oxidized, and the 5'-protecting group is removed (deprotection). The dinucleotide is then ready for coupling with another nucleoside monomer having a 3'-phosphoramidite and a 5'-protecting group. These steps are repeated until the oligonucleotide reaches the desired length and/or sequence.

As such, aspects of the invention include methods of synthesizing nucleic acids that include the steps of providing a nucleoside residue having an unprotected hydroxyl group and a 2' protected nucleoside monomer, wherein the 2' protected nucleoside monomer comprises a silyl containing thiocarbonate protecting group; and contacting the nucleoside residue and the 2' protected nucleoside monomer under conditions sufficient to covalently bond the 2' protected nucleoside monomer to the nucleoside residue to produce a nucleic acid. The above describes a single monomer addition step of the synthesis protocol, where the above process is reiterated with additional monomers as desired to produce a polymer of desired length and sequence. As reviewed above, between each monomer addition step, the process may include exposing the nucleic acid to an oxidizing and deprotecting agent.

In certain embodiments, the 2' protected monomer has the structure of Formula (I), with the same limitations on Formula (I) as described above.

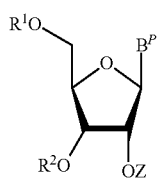

I

In additional embodiments, Z has the structure of Formula (II), with the same limitations on Formula (II) as described above.

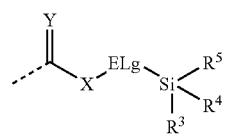

II

In additional embodiments, Z has the structure of Formula (Va) or Formula (Vb).

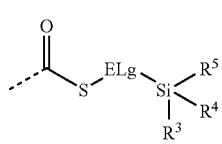

Va

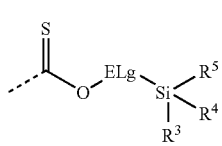

Vb

In certain embodiments, $R^2$ is a hydroxyl protecting group, and $R^1$ has the structure of Formula (VIII):

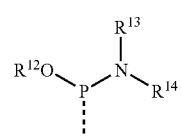

VIII wherein:
$R^{12}$, $R^{13}$, and $R^{14}$ are each independently selected from the group consisting of hydrocarbyl, substituted hydrocarbyls, aryls, and substituted aryls.

In other embodiments, $R^1$ is a hydroxyl protecting group, and $R^2$ has the structure of Formula (VIII).

Protecting groups of the invention, on the 2' hydroxyl, and optionally on the base, allow synthesis of long sequences of RNA which were not possible to synthesize chemically before, because of the ease and efficiency of removing these protecting groups. The oligonucleotides synthesized by embodiments of the methods disclosed herein are 20, 25, 30, 35, 40, 45, 50, 55, 60, 65, 70, 75, 80, 85, 90, 95, 100, 105, 110, 115, 120, 125, 130, 135, 140, 145 or 150 nucleotides in length or longer. Furthermore, an oligonucleotide synthesized according to this invention can be combined with another oligonucleotide to form a longer oligonucleotide. For example, an oligonucleotide of 70 bases can be coupled with another oligonucleotide of 70 bases by chemical ligation. As another example, two oligonucleotides can be ligated with an RNA ligase. In this case, the 2'-protecting groups should be removed before ligation.

Following synthesis of the nucleic acids in accordance methods of the invention, e.g., as described above, the 2' protecting groups may be removed, as desired, to produce a nucleic acid product with unprotected 2' OH moieties. As such, certain embodiments of the methods further include removing the 2' hydroxyl protecting group by incubating the nucleic acid with a nucleophile. The conditions used to remove 2' protecting groups after the synthesis of RNA include, but are not limited to, the following illustrative conditions. Solutions containing TBAF (tetrabutylammonium fluoride) are employed in certain embodiments, while in other embodiments solutions of HF/TEMED or HF/TEA (triethylamine) may be employed. Deprotection of carbamates with TBAF has been reported recently (Jacquemard et al., Tetrahedron 60: 10039-47 (2004)). Desilylation with TBAF was reported by Oda et al. Tetrahedron 41: 3257-68 (1985). TBAB (tetrabutylammonium bromide) has also worked successfully. In certain embodiments, e.g., where 1% of tBuOOH or $H_2O_2$ is added to HF/TEMED or HF/TEA with a pH between 5.1 and 6.8, the removal of protecting groups is accomplished within 4 hours or less. The protecting groups can also be removed using Lewis acids under anhydrous conditions such as zinc bromide or $BF_3$ etherate or several other lewis acids as described in Claudio J. Salomon, Ernesto G. Mata and Oreste A. Mascaretti Tetrahedron Volume 49, Issue 18, 30 Apr. 1993, Pages 3691-3734, the disclosure of which acids are incorporated herein by reference. The protecting groups are particularly susceptible to Lewis acid cleavage due to the electronic effect of the silyl group. If the cleavage is done under anhydrous conditions, the conditions minimize or eliminate the effect of isomerization of the internucleotide bond that can occur in the presence of aqueous acids. These reactions may be done in polar solvents due to the solubility of typical Lewis acids and the reactions can be done while the RNA sequences are attached to support, adsorbed to support or in solution. In a similar fashion Ferreira et. al. demonstrated that silyl protecting groups can be removed from the hetrobases using zinc bromide (*Nucleosides, Nucleotides and Nucleic Acids,* 2005, 24 (5-7), 1009-1013 Sp. Iss; *Tetrahedron Letters* 2004, 45 (33), 6287-6290). Care is taken when employing these conditions to avoid conditions that cause RNA degradation.

In some embodiments of this invention, the nucleoside monomers contain bases that are protected by the same protecting group as the 2'-OH, thus both of these protecting groups can be removed at the same time.

As reviewed above, certain embodiments of the invention are solid phase synthesis embodiment, i.e., where the synthetic methods of the invention are conducted on a solid support having a surface to which chemical entities may bind. The solid support may vary widely in terms of form and composition, as illustrated by the discussion below. Examples of solid supports include beads or analogous objects, planar supports, e.g., as employed in array fabrication, etc.

In some embodiments, multiple oligonucleotides being synthesized are attached, directly or indirectly, to the same solid support and may form part of an array. An "array" is a collection of separate molecules each arranged in a spatially defined and a physically addressable manner. The number of molecules, or "features," that can be contained on an array will largely be determined by the surface area of the substrate, the size of a feature and the spacing between features, wherein the array surface may or may not comprise a local background region represented by non-feature area. Generally, arrays can have densities of up to several hundred thousand or more features per $cm^2$, such as about 2,500 to about 200,000 features/$cm^2$. The features may or may not be covalently bonded to the substrate. An "array," or "chemical array" used interchangeably includes any one-dimensional, two-dimensional or substantially two-dimensional (as well as a three-dimensional) arrangement of addressable regions bearing a particular nucleic acids associated with that region. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features may be separated by intervening spaces. In the case of an array, the "target" will be referenced as a moiety in a mobile phase (e.g., fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

In some other embodiments, oligonucleotides being synthesized are attached to a bead directly or indirectly. Suitable solid supports may have a variety of forms and compositions and derive from naturally occurring materials, naturally occurring materials that have been synthetically modified, or synthetic materials. Examples of suitable support materials include, but are not limited to, silicas, teflons, glasses, polysaccharides such as agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like. The initial monomer of the oligonucleotide to be synthesized on the substrate surface may be bound to a linking moiety which is in turn bound to a surface hydrophilic group, e.g., a surface hydroxyl moiety present on a silica substrate. In some embodiments, a universal linker is used. In some other embodiments, the initial monomer is reacted directly with, e.g., a surface hydroxyl moiety. Alternatively, oligonucleotides can be synthesized first according to the present invention, and attached to a solid substrate post-synthesis by any method known in the art. Thus, the present invention can be used to prepare arrays of oligonucleotides wherein the oligonucleotides are either synthesized on the array, or attached to the array substrate post-synthesis.

In certain embodiments, the method further includes cleaving the nucleic acid from the solid support to produce a free nucleic acid. Cleavage may occur using any convenient cleavage conditions that serve to break the covalent bond between the terminal residue or region of the synthesized product nucleic acid and the support, while at the same time preserving the product nucleic acid. The specific conditions employed will depend, at least in part, on the nature of the product nucleic acid including any protecting groups therein, the nature of the linkage of the product nucleic acid to the support, and the like. In this step of the subject methods, the solid support is subjected to cleavage conditions sufficient to cleave the immobilized first nucleic acids of the features from the substrate surface. Generally, this step comprises contacting the array with an effective amount of a cleavage agent. The cleavage agent will, necessarily, be chosen in view of the particular nature of the cleavable region of the cleavable domain that is to be cleaved, such that the region is labile with respect to the chosen cleavage agent. Where the cleavable domain comprises a photocleavable or photolabile group, cleavage can be effectuated by subjecting the cleavable domain to light of the appropriate wavelength sufficient to cleave the cleavable region. Likewise, for chemically cleavable moieties, the array can be contacted with a chemical capable of cleaving the linker, e.g. the appropriate acid or base, depending on the nature of the chemically labile moiety. Suitable cleavable sites include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyldialkoxysilyl (cleavable by fluoride ions). Other cleavable sites will be apparent to those skilled in the art or are described in the pertinent literature and texts (e.g., Brown (1997) Contemporary Organic Synthesis 4(3); 216-237). Similarly, in those embodiments where the cleavable domain includes a restriction endonuclease recognized sequence, the array is contacted with an effective amount of the appropriate restriction endonuclease that recognizes and cleaves the sequence.

With the efficiency and ease of the present method, oligonucleotide synthesis can be performed in small or large scales. The quantity of oligonucleotide made in one complete run of the present method (in one container) can thus be less than a microgram, or in micrograms, tens of micrograms, hundreds of micrograms, grams, tens of grams, hundreds of grams, or even kilograms.

In addition to their use in nucleoside monomers and nucleic acid synthesis, the protecting groups of the invention can be used advantageously in other molecules in which it is desired to protect a 1,2- or 1,3-diol moiety while minimizing cyclic carbonate formation. For example, the structures shown below will be resistant to cyclic carbonate formation:

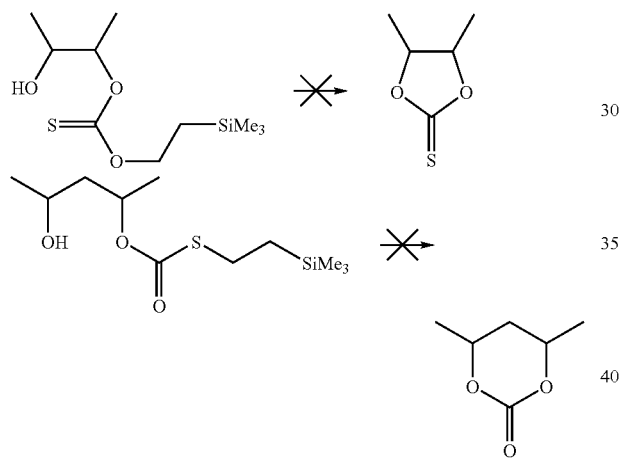

It is demonstrated above that selective removal of TIPS can be achieved in the presence of a protecting group of the invention. The protecting group can also be used for the regioselective deprotection of an alcohol that has a siloxane protecting group other than TIPS, such as TBDMS, trimethylsilyl, triethylsilyl, and triisopropylsilyl, while not removing the protecting group. The alcohol being protected can be a molecule other than a nucleoside monomer or oligonucleotide. For example, in the structure shown below, the siloxane protected alcohol can be deprotected selectively in the presence of the protected alcohol.

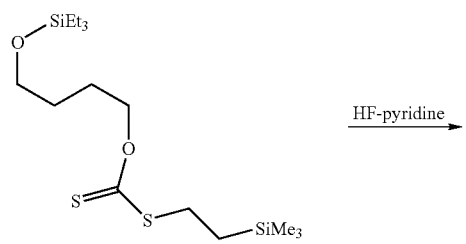

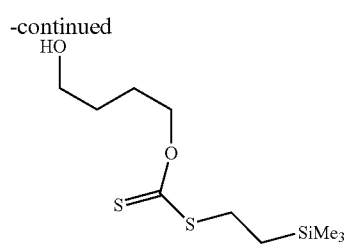

The combination of a silyl containing thiocarbonate protecting group with another siloxane protecting group, such as TIPS, thus offers a convenient method of hydroxyl group differentiation for molecules with more than one hydroxyl group. Such molecules are not limited to nucleoside monomers and oligonucleotides. For example, the combination of protecting groups can be used in intermediates during the synthesis of carbohydrates:

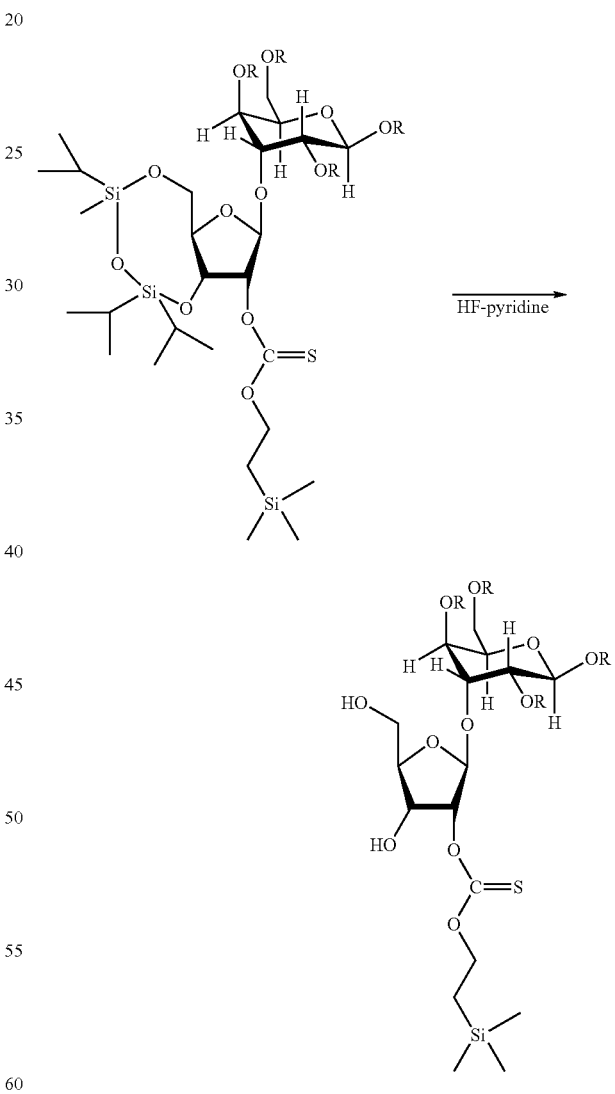

Nucleic Acid Products

Aspects of the invention further include the nucleic acid products of the methods of the invention. The nucleic acid products, e.g., RNA, of the methods of the invention may vary in size, ranging in certain embodiments from 2 to 200 or more monomeric units in length, such as 2 to 100 or more monomeric units in length, including 2 to 50 or more monomeric units in length. In certain embodiments, the size of the product nucleic acids ranges from 2 to 25 monomeric units in length, e.g., 15 to 25 monomeric units in length, such as 17 to 23 monomeric units in length, including 19, 20, 21, or 22 monomeric units in length.

In certain embodiments, nucleic acid products of the invention have the structure of Formula (VI):

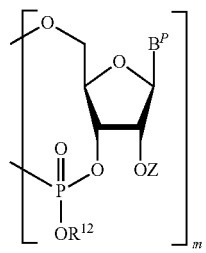

VI wherein:

$B^P$ is a protected or unprotected nitrogen-containing base;

Z is a silyl containing thiocarbonate protecting group;

$R^{12}$ is selected from the group consisting of hydrogen, hydrocarbyls, substituted hydrocarbyls, aryls, and substituted aryls; and m is an integer greater than 1.

In additional embodiments of nucleic acids, Z has the structure of Formula (II) with the same limitations on Formula (II) as described above.

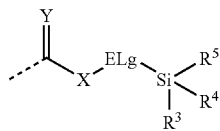

(II)

In additional embodiments, the nucleic acid has the structure of Formula (VIIa) or Formula (VIIb).

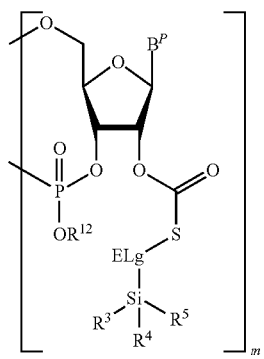

VIIa

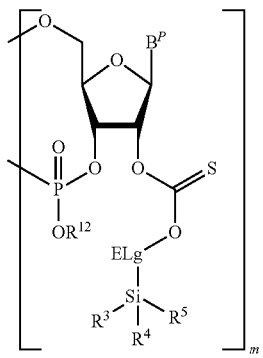

VIIb

In additional embodiments, the nucleic acids have the above structures except that the Z protecting group has been removed, producing a free nucleic acid in which the Z group is replaced by H.

Applications

The product nucleic acids produced in accordance with methods of the invention find use in a variety of applications, including research, diagnostic and therapeutic applications. For example, the product nucleic acids find use in research applications, e.g., as probes, primers, etc. With respect to diagnostic applications, the product nucleic acids may also find use as probes, primers, or other agents employed in diagnostic protocols. With respect to therapeutic applications, the product nucleic acids find use as any DNA, RNA or other nucleic acid therapeutic, such as antisense nucleic acids, in gene therapy applications, interfering RNA (i.e., iRNA or RNAi) applications, etc.

Depending on the application for which the nucleic acids are synthesized, the nucleic acids may or may not be modified in some manner following their synthesis. As such, in certain embodiments the product nucleic acids are not further modified following synthesis. In yet other embodiments, the nucleic acids are modified in some manner following their synthesis.

A variety of different modifications may be made to the product nucleic acids as desired. For example, where the product nucleic acids are interfering ribonucleic acids (iRNA), a variety of post-synthesis modifications may be desirable. The iRNA agent can be further modified so as to be attached to a ligand that is selected to improve stability, distribution or cellular uptake of the agent, e.g., cholesterol. The following post-synthesis modifications are described for convenience primarily in terms of iRNA embodiments. However, such modifications are readily adapted to DNA embodiments and the following description encompasses such embodiments as well.

The following modifications may be made before or after cleavage of the nucleic acid from the support, as desired.

Unmodified RNA refers to a molecule in which the components of the nucleic acid, namely sugars, bases, and phosphate moieties, are the same or essentially the same as that which occur in nature, e.g., as occur naturally in the human body. The art has referred to rare or unusual, but naturally occurring, RNAs as modified RNAs, see, e.g., Limbach et al., (1994) Nucleic Acids Res. 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, e.g., different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. For example, a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g., pharmacodynamic properties, which are further discussed below. Other suitable modifications to a sugar, base, or backbone of an iRNA agent are described in PCT Application No. PCT/US2004/01193, filed Jan. 16, 2004. An iRNA agent can include a non-naturally occurring base, such as the bases described in PCT Application No. PCT/US2004/011822, filed Apr. 16, 2004. An iRNA agent can include a non-naturally occurring sugar, such as a non-carbohydrate cyclic carrier molecule. Exemplary features, of non-naturally occurring sugars for use in iRNA agents are described in PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in PCT Application No. PCT/US2004/07070 filed on Mar. 8, 2004.

An iRNA agent can include ligand-conjugated monomer subunits and monomers for oligonucleotide synthesis. Exemplary monomers are described in U.S. application Ser. No. 10/916,185, filed on Aug. 10, 2004. An iRNA agent can have a ZXY structure, such as is described in PCT Application No. PCT/US2004/07070 filed on Mar. 8, 2004. An iRNA agent can be complexed with an amphipathic moiety. Exemplary amphipathic moieties for use with iRNA agents are described in PCT Application No. PCT/US2004/07070 filed on Mar. 8, 2004.

In another embodiment, the iRNA agent can be complexed to a delivery agent that features a modular complex. The complex can include a carrier agent linked to one or more of (such as two or more, including all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in PCT Application No. PCT/US2004/07070 filed on Mar. 8, 2004.

An iRNA agent can have enhanced resistance to nucleases. For increased nuclease resistance and/or binding affinity to the target, an iRNA agent, e.g., the sense and/or antisense strands of the iRNA agent, can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEGs), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage, as described in U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3'

(5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of the oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of the oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In some embodiments, the nucleotide overhang includes 1 to 4 unpaired nucleotides, in other embodiments 2 to 3 unpaired nucleotides. In one embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In certain embodiments, the nucleotide overhang is on the 3'-end of the antisense strand. In one embodiment, the iRNA agent includes the motif 5'-CGC-3' on the 3'-end of the antisense strand, such that a 2-nucleotide overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization may be used only in terminal regions, and not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In certain embodiments, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nucleotide antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

The properties of an iRNA agent, including its pharmacological properties, can be influenced and tailored, for example, by the introduction of ligands, e.g. tethered ligands. A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Of interest are ligands, which are coupled, e.g., covalently, either directly or indirectly via an intervening tether, to the carrier. In certain embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Ligands of interest can improve transport, hybridization, and specificity properties and may also improve nuclease resistance of the resultant natural or modified oligoribonucleotide, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent. e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetylglucosamine, multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. Also of interest are the lipid modifications described in WO/2005/023994; the disclosure of which is herein incorporated by reference.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, a helical cell-permeation agent. In some embodiments, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent may be an alpha-helical agent, which may have a lipophilic and a lipophobic phase.

In certain embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophsphate $((HO)_2(O)P—O-5')$; 5'-diphosphate $((HO)2(O)P—O—P(HO)(O)—O-5')$; 5'-triphosphate $((HO)_2(O)P—O—(HO)(O)P—O—P(HO)(O)—O-5')$; 5'-guanosine cap (7-methylated or non-methylated) $(7m-G-O-5'-(HO)(O)P—O—(HO)(O)P—O—P(HO)(O)—O-5')$; 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Where desired, the nucleic acid, e.g., iRNA. DNA, etc. agents described herein can be formulated for administration to a subject, such as parenterally, e.g. via injection, orally, topically, to the eye, etc. As such, the nucleic acid can be combined with a pharmaceutically acceptable vehicle to provide a pharmaceutical composition. For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation. The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as Mg24), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences.

The nucleic acids can be formulated into pharmaceutical compositions by combination with appropriate, pharmaceutically acceptable vehicles, i.e., carriers or diluents, and may be formulated into preparations in solid, semi solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Nucleic acids may also be introduced into tissues or host cells by other routes, including microinjection, or fusion of vesicles. Jet injection may also be used for intra-muscular administration, as described by Furth et al. (1992), Anal Biochem 205:365-368. The nucleic acids may be coated onto gold microparticles, and delivered intradermally by a particle bombardment device, or "gene gun" as described in the literature (see, for example, Tang et al. (1992), Nature 356:152 154), where gold microprojectiles are coated with the DNA, then bombarded into skin cells. Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc. See e.g., the viral and non-viral mediated delivery protocols described above. Accordingly, of interest are pharmaceutical vehicles for use in such delivery methods.

The ribonucleic acids produced by embodiments of the methods find use in a variety of different applications, including but not limited to differential gene expression analysis, gene-silencing applications, nucleic acid library generation applications and therapeutic applications (e.g., in the production of antisense RNA, siRNA, etc.) Additional details regarding these types of utilities for RNA produced according to embodiments of the invention are provided in pending U.S.

patent application Ser. No. 10/961,991 titled "Array-Based Methods for Producing Ribonucleic Acids," filed on Oct. 8, 2004 and published as US-2006-0078889-A1 on Apr. 13, 2006; the disclosure of which is herein incorporated by reference.

Kits

Also of interest are kits for use in practicing certain embodiments of the invention. In certain embodiments, kits include at least 2 different protected monomers, e.g., 2' silyl containing thiocarbonate protected monomers in accordance with the invention, where the kits may include the monomers that have the same nucleobase or monomers that include different nucleobases, e.g., A, G, C and U. The kits may further include additional reagents employed in methods of the invention, e.g., buffers, oxidizing agents, capping agents, cleavage agents, etc. In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples illustrate the synthesis of compounds of the present invention, and are not intended to limit the scope of the invention set forth in the claims appended hereto.

EXPERIMENTAL

Example 1

Synthesis of 5',3'-O-(Tetraisopropyldisiloxane-1,3-diyl) 2'-O-(p-nitrophenyl)oxycarbonyl protected uridine 5',3'-O-(Tetraisopropyldisiloxane-1,3-diyl) uridine (15 millimoles (mmole)) was coevaporated 3 times with pyridine, and then dried on vacuum pump for 12 hours (h). Anhydrous pyridine (150 milliliters (mL)), DMAP (6 mmole) and p-nitrophenyl chloroformate (22.5 mmole) were added, and the mixture was stirred at room temperature for 16 hours. The product was purified by flash chromatography using hexanes with a gradient of ethyl acetate (EtOAc) (0-60%).
Yield 100%
ESI MS: 658 (M+Li), 686 (M+Cl)

This example illustrates regioselectively protecting the 2' hydroxyl group of a nucleoside with a carbonate protecting group.

Example 2

Synthesis of 5',3'-O-(Tetraisopropyldisiloxane-1,3-diyl) 2'-O-t-butylthiocarbonyl (BSC) uridine 5',3'-O-(Tetraisopropyldisiloxane-1,3-diyl) 2'-O-(p-nitrophenyl)carbonate protected uridine (15 mmole) was coevaporated 3 times with pyridine, and then dried on vacuum pump for 4 hours. Anhydrous pyridine (150 mL) and sodium 2-methyl-2-propanethiolate (24 mmole) were added, and the mixture was stirred at room temperature for 16 hours. The product was purified by column chromatography using hexanes with a gradient of EtOAc (0-30%). Yield 76.4% ESI MS: 609 (M+Li), 637 (M+Cl)

This example illustrates transforming a carbonate protecting group into a thiocarbonate protecting group.

Example 3

Synthesis of 5',3'-O-(Tetraisopropyldisiloxane-1,3-diyl) 2'-O-Ethylthiocarbonyl (ESC) uridine 5',3'-O-(Tetraisopropyldisiloxane-1,3-diyl)uridine (15 mmole) was coevaporated 3 times with pyridine, and then dried on vacuum pump for 12 hours. Anhydrous pyridine (150 mL), and ethyl chlorothioformate (18 mmole) were added, and the mixture was stirred at room temperature for 16 hours. The product was purified by column chromatography using hexanes with a gradient of chloroform (50-100%).
Yield 74.3%
ESI MS: 581 (M+Li), 609 (M+Cl)

This example illustrates regioselectively protecting the 2' hydroxyl group of a nucleoside with a thionyl carbonate protecting group.

Example 4

Removal of the TIPS

2'-O-thiocarbonate protected uridines

Hydrogen fluoride-pyridine complex (HF:Py 7:3, 7 mL) was carefully added to an ice-cold solution of pyridine (8 mL) in acetonitrile (46.5 mL). The pyridine-HF reagent so formed (32 mL) was then transferred to a flask charged with 5',3'-O-(tetraisopropyldisiloxane-1,3-diyl) 2'-O-carbonate protected uridine (10 mmole), and the mixture was stirred at room temperature for 2 hours. The reaction was quenched with 5% solution of calcium chloride in water (300 mL). Crude product was extracted with EtOAc (3-5 times), and dried with anhydrous $Na_2SO_4$. After filtration, the organic layer was concentrated to dryness and left under pump vacuum for 16 hours.
Yield 85-100%
ESI MS:
BSC analog: 361 (M+1), 383 (M+Na), 399 (M+K)
ESC analog: 333 (M+1), 355 (M+Na), 371 (M+K)

This example illustrates the lack of rearrangement of the 2' carbonate or thiocarbonyl carbonate protecting group while deprotecting the 3' (and 5') hydroxyl groups of a nucleoside.

Example 5

Synthesis of 5'-O-DMT 2'-O-thiocarbonyl protected uridine 3'-O-[methyl-(N,N-diisopropyl)]-phosphoramidites 2'-O-thiocarbonate protected uridine (3 mmole) was dried on a vacuum pump for 6 hours. Anhydrous THF (30 mL), 2,4,6-collidine (22.5 mmole) and dimethoxytrityl chloride (3.3 mmole) were added, and the mixture was stirred at room temperature until TLC ($CHCl_3$/MeOH 9:1) showed full disappearance of nucleoside substrate (16-24 hours). 2,4,6-Collidine (3 mmole) and 1-methylimidazole (1.5 mmole) were added in one portion and N,N-diisopropylmethylphosphonamidic chloride was added slowly to the reaction mixture over 10-15 minutes (min). The reaction mixture was then stirred for another 2 hours. The solvent was removed in vacuo, and the crude product was purified by column chromatography using hexanes with a gradient of EtOAc (0-50%).
Yield 60-65%

| ESI MS: | |
|---|---|
| ESC monomer: | 802 (M + Li), 830 (M + Cl) |
| BSC monomer: | 830 (M + Li), 858 (M + Cl) |
| $^{31}$P NMR (CDCl$_3$): | |
| ESC monomer: | 152.33, 151.72 |
| BSC monomer: | |

This example illustrates protection of the 5' hydroxide and formation of a 3' phosphoramidite in a 2' carbonyl or thiocarbonyl protected nucleoside.

Example 6

Synthesis of 5',3'-O-(Tetraisopropyldisiloxane-1,3-diyl) 2'-O-Ethylthiocarbonyl (ESC) N$^4$-phenyloxycarbonyl cytidine 5',3'-O-(tetraisopropyldisiloxane-1,3-diyl)ribocytidine (10 mmole, 4.85 grams (g)) was dried by coevaporation with dry pyridine. This compound was dissolved in 100 mL of dry pyridine and trimethylchlorosilane (5 equivalents (eq), 50 mmole, 6.34 mL) was added. The mixture was stirred at room temperature for 2 hours and phenylchloroformate was added (1.2 eq, 12 mmole, 1.51 mL). The reaction was stirred at room temperature for 2 hours. The excess chloroformate was quenched by adding 2 mL of methanol. The mixture was diluted with a saturated solution of sodium bicarbonate in water. This mixture was extracted with dichloromethane. The organic layer was then dried over sodium sulfate and evaporated to dryness.

The crude product of this reaction was diluted in 160 mL of dichloromethane and 5.7 g of p-toluenesulfonic acid in 30 mL of THF. The reaction was stirred at room temperature for 15 minutes. The reaction was quenched by adding 200 ml of a saturated aqueous solution of sodium bicarbonate. This mixture was extracted with dichloromethane, the organic layer was dried over sodium sulfate and evaporated to dryness.

The crude product was dried by coevaporation with dry pyridine, dissolved in 100 ml of dry pyridine, and ethylchlorothioformate (1.7 eq, 1.76 mL) and DMAP (0.1 eq, 0.122 g) were added. The reaction was stirred at room temperature overnight, then diluted with a saturated aqueous solution of sodium bicarbonate. This mixture was extracted with dichloromethane, the organic layer was dried over sodium sulfate and evaporated to dryness. The crude product was purified by column chromatography (cyclohexane/ethylacetate 75/25). The product was obtained as a foam (4 g, 60% over 4 steps).
$^1$H NMR 400 MHz (CDCl$_3$): 8.2 (s, 1H); 7.45-7.2 (m, 5H); 5.95 (s, 1H); 5.55 (d, 1H); 4.35 (m, 1H); 4.3 (d, 1H); 4.2-3.95 (m, 2H); 2.95-2.8 (m, 2H); 1.3 (t, 3H); 1.15-0.95 (m, 27H)
Mass spectrum ESI: 700.2274 [M+Li]$^+$ This example illustrates taking a 3', 5' TIPS protected nucleoside, protecting the base group, and protecting the 2' hydroxide with a thiocarbonate protecting group.

Example 7

Removal of TIPS

Synthesis of 2'-O-ethylthiocarbonyl N$^4$-phenyloxycarbonyl Cytidine

5',3'-O-(Tetraisopropyldisiloxane-1,3-diyl) 2'-O-ethylthiocarbonate N$^4$-phenylcarbamate Cytidine (2.57 g, 5.7 mmole) was dried by coevaporation with dry acetonitrile, then diluted in 40 ml of dry acetonitrile and the HF/pyridine (30 eq of HF, 4.33 mL) was added and the reaction was stirred at room temperature for 5 h. The fluoride was quenched by adding a solution of CaCl$_2$ and the product was extracted with dichloromethane. The organic layer was dried over sodium sulfate and evaporated to dryness.

The crude product was coevaporated with dry acetonitrile, then dissolved in 40 mL of dry THF and 10 eq (7.55 mL) of 2,4,6-collidine was added to the mixture. DMTCl (1.2 eq, 2.31 g) was added and the reaction was stirred at room temperature for 3 h 30.5 more equivalents of 2,4,6-collidine (3.3 ml), 0.5 eq (0.22 mL) of N-methylimidazole and 2.5 eq (2.75 mL) of N,N-diisopropylmethyl-phosphonamidic chloride were added. The resulting mixture was stirred at room temperature for 4 h. The mixture was diluted with a saturated aqueous solution of sodium bicarbonate and extracted with dichloromethane. The organic layer was dried over sodium sulfate and evaporated to dryness. The crude product was purified by column chromatography (hexane/ethylacetate/pyridine 75/20/5 to 20/75/5). The product was obtained as a slightly yellow foam (1.64 g, 31% over 3 steps).
$^{31}$P NMR 400 MHz (CD$_3$CN): 151.709-151.325
Mass spectrum ESI: 921.332 [M+Li]$^+$ This example illustrates the removal of TIPS from the 3' and 5' hydroxide groups of a nucleoside with a 2' thionyl carbonate protecting group and a protected base, followed by 5' protection with DMT and formation of a 3' phosphoramidate.

Example 8

Protection of the Exocyclic Adenosyl Amino Group

5',3'-O-(tetraisopropyldisiloxane-1,3-diyl)adenosine (3.9 mmole, 2 g) was coevaporated twice with dry pyridine. This compound was dissolved in 20 ml of dry pyridine and trimethylchlorosilane (5 eq, 19.6 mmole, 2.48 mL) was added. The mixture was stirred at room temperature for 30 min and phenylchloroformate was added (2 eq, 7.84 mmole, 0.98 mL). The reaction was stirred at room temperature for 2 hours. Then, 5 mL of water was added, and the mixture was stirred at room temperature for another 2 hours. The reaction was then diluted with a saturated aqueous solution of sodium bicarbonate. This solution was extracted with dichloromethane. The organic layer was dried over sodium sulfate and evaporated to dryness. The crude was purified by column chromatography (CH$_2$Cl$_2$/MeOH 90/10). The product was obtained as white foam (0.62 g, 25%)
$^1$H NMR 400 MHz (CDCl$_3$): 9.85 (s, 1H); 8.75 (s, 1H); 8.2 (s, 1H); 7.4-7.2 (m, 5H); 6.05 (s, 1H); 5.05 (m, 1H); 4.65 (d, 1H); 4.15-4 (m, 4H); 3.75 (s, 1H); 1.15-0.95 (m, 27H)

This example illustrates a method of protecting an exocyclic amine on the base of a 3,5 TIPS protected nucleoside.

Example 9

Synthesis of 5'-O-DMT-2'-O-ethylthiocarbonyl-3'-O-[methyl-(N,N-diisopropyl)]-phosphoramidite-N$^6$-phenyloxycarbonyl Adenosine 5',3'-O-(tetraisopropyldisiloxane-1,3-diyl) N$^6$-phenyloxycarbonyl adenosine (0.62 g, 1 mMole) was dried by coevaporation with anhydrous pyridine, and dissolved in 5 mL of dry pyridine. Ethychlorothioformate (1.7 eq, 2 mmole, 0.208 mL) and DMAP (0.1 eq, 0.012 g) were added. The reaction was stirred at room temperature overnight, then diluted with a saturated aqueous solution of sodium bicarbonate. The crude reaction mixture was extracted with dichloromethane. The organic layer was dried over sodium sulfate and evaporated to dryness.

The crude product was dried by coevaporation with dry acetonitrile, and then diluted in 5 mL of dry acetonitrile. HF/pyridine (30 eq of HF, 0.375 mL) was added and the reaction was stirred at room temperature for 5 hours. The fluoride was quenched by adding a solution of $CaCl_2$ and the product was extracted with dichloromethane. The organic layer was dried over sodium sulfate and evaporated to dryness.

The crude product was dried by coevaporation with dry acetonitrile, then 5 mL of dry THF and 10 eq (1.35 mL) of 2,4,6-collidine were added. DMTCl (1.2 eq, 0.4 g) was added and the reaction was stirred at room temperature for 2 hours. 5 more equivalents of 2,4,6-collidine (0.7 mL), 0.5 eq (0.039 mL) of N-methylimidazole and 2.5 eq (1.45 mL) of N,N-diisopropylmethyl-phosphonamidic chloride were added. The reaction was stirred at room temperature for 2 hours. The mixture was diluted with a saturated aqueous solution of sodium bicarbonate and extracted with dichloromethane. The organic layer was dried over sodium sulfate and evaporated to dryness. The crude product was purified by column chromatography (hexane/ethylacetate/pyridine 75/20/5 to 20/75/5). The product desired was obtained as a white foam.

$^{31}$P NMR 400 MHz ($CDCl_3$): 152.925-152.040

This example illustrates the removal of TIPS from the 3' and 5' hydroxide groups of a nucleoside with a 2' thionyl carbonate protecting group and a protected base, followed by 5' protection with DMT and formation of a 3' phosphoramidate.

Example 10

General Procedure for Synthesis of Oligouridines on a Solid Support

All syntheses were performed on a 1 micromolar (uM) scale using dT-Q-CPG columns from Glen Research according to standard RNA cycle. For coupling step phosphoramidite and tetrazole were delivered to the synthesis column and left for 10 minutes.

After completion of all synthesis steps, the product mixture (still joined to CPG) was treated with a 1 molar (M) solution of disodium 2-carbamoyl-2-cyanoethylene-1,1-dithiolate in DMF (1 mL) for 30 minutes at room temperature, and then washed with water followed by acetonitrile and dried under argon.

Oligomers were cleaved from solid support and deprotected by treatment with 1 M TBAF solution in THF (1 mL). For $U_4T$ pentamers, deprotection was completed within 1 hour (ESC protection) and 6 hours (BSC protection).

Reactions were quenched with 0.1 M TEAA, desalted on Poly-pak cartridges using standard procedure, and evaporated to dryness. The resulting reaction products were dissolved in water and analyzed by HPLC [ODS-Hypersil (5 m), column 4.0×250, flow 1.5 mL/min, 0-20% MeCN in 50 mM TEAB (linear gradient) in 40 min].

In some cases oligomers were cleaved from the solid support (no 2'-deprotection) by treatment with TEMED/HF/MeCN mixture (2:1:7, 1 mL) for 40 minutes at room temperature. Reactions were quenched, desalted analyzed as mentioned before.

Example 11

Synthesis of 2'-O-BEST Uridine

Hydrogen fluoride pyridine complex (7:3, 3 5 mL) was added to an ice-cold solution of pyridine (4 mL) in acetonitrile (23 mL). The resultant deprotection mixture (29 mL) was transferred to the flask with 3',5'-O-TIPS-2'-BEST uridine (9.0 mmole), and the mixture was left with stirring at room temperature for 2 hours. Reaction was quenched with 5% aqueous $CaCl_2$ (300 mL). The product was extracted (3 times) with EtOAc. The organic layer was dried with $Na_2SO_4$. Yield 100%; ESI MS: 427 (M+Na), 809 (dimer+1), 831 (dimer+Na), 439 (M+Cl)

Example 12

Synthesis of 5'-O-DMT-2'-O-BEST Uridine 3'-O—[(O-Methyl)-(N,N,-diisopropyl)]-phosphoramidite 2'-BEST uridine (9 mmole) was dried on vacuum pump, and then dissolved in THF (90 mL). 2,3,5-Collidine (7.5 eq) and DMT-Cl (1.25 eq) were added, and the reaction mixture was stirred at room temperature. 2,3,5-Collidine (1 eq) and N-Methylimidazole (0.5 eq) were then added. Methyl-(N,N-diisopropylamino)phosphonamidic chloride (2.5 eq) was then added dropwise over 10 minutes at room temperature. The reaction mixture was left with stirring at room temperature for ~2 hours. The solvent was removed in vacuo, and the crude product was purified by column chromatography using hexanes:$Et_3N$ (99.9:0.1) with a gradient of EtOAc (0-40%). Yield 34.4%; $^{31}$P NMR (CD3CN): 150.66, 150.51; ESI MS: 868 (M+1), 890 (M+Na)

Example 12

Synthesis of U4T on Solid Support

General Procedure

Figure 2:
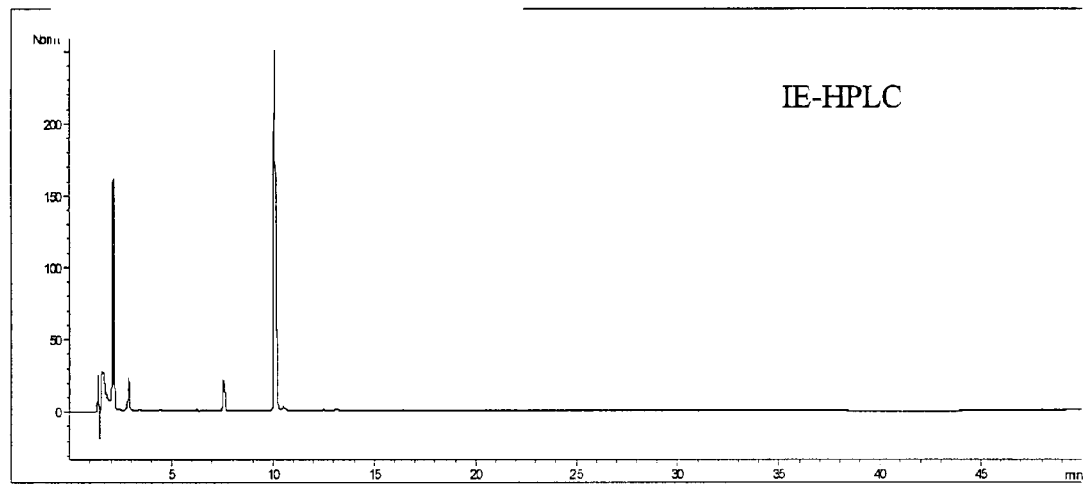
Figure 2:
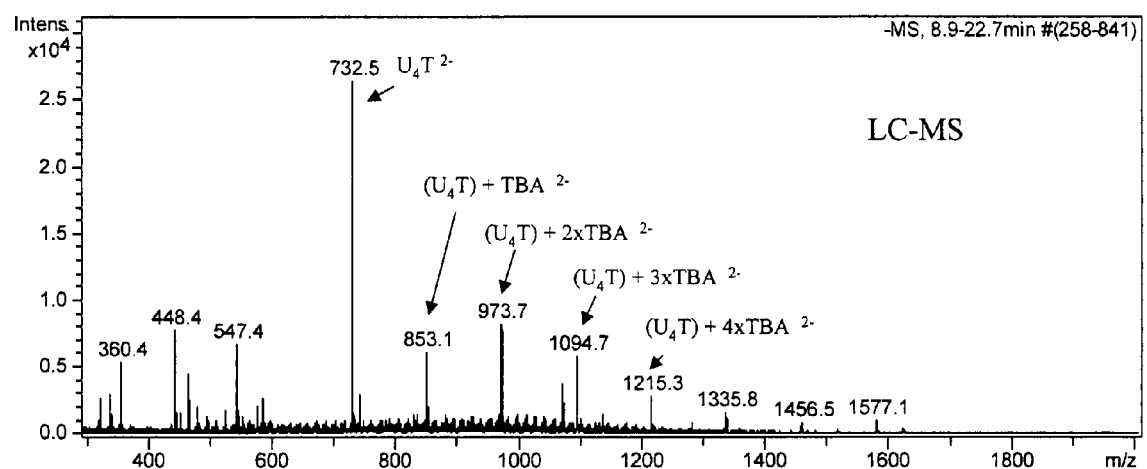
Figure 3:
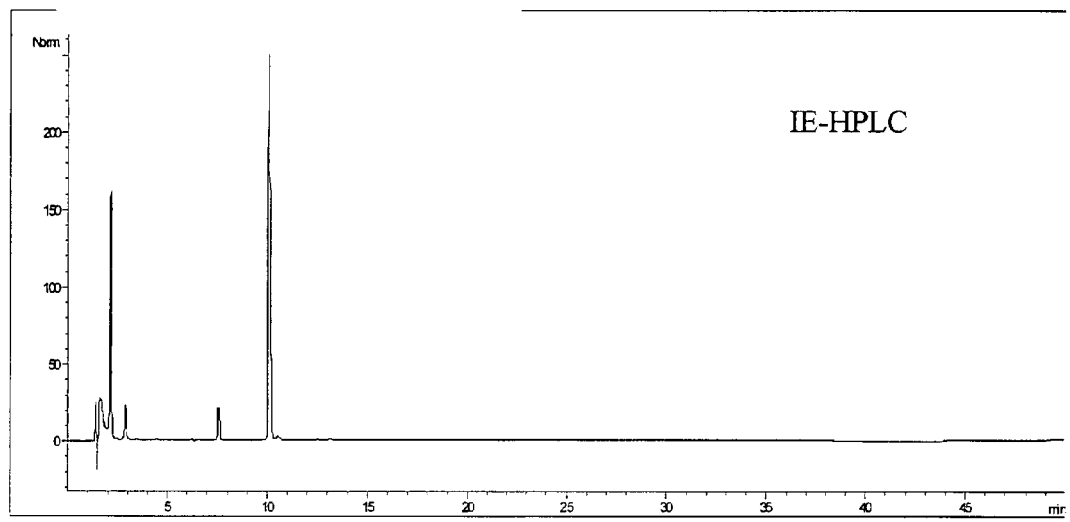
Figure 3:
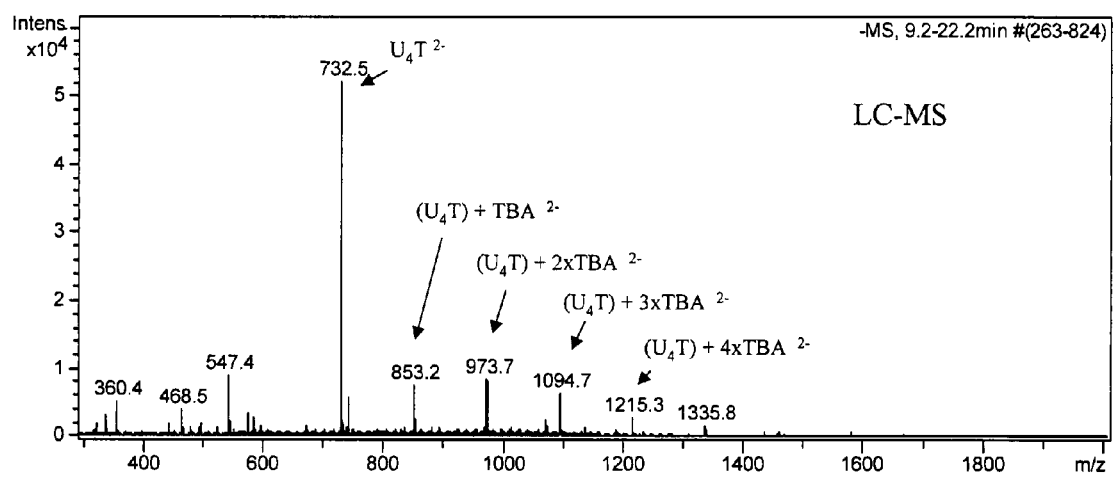
Figure 4:
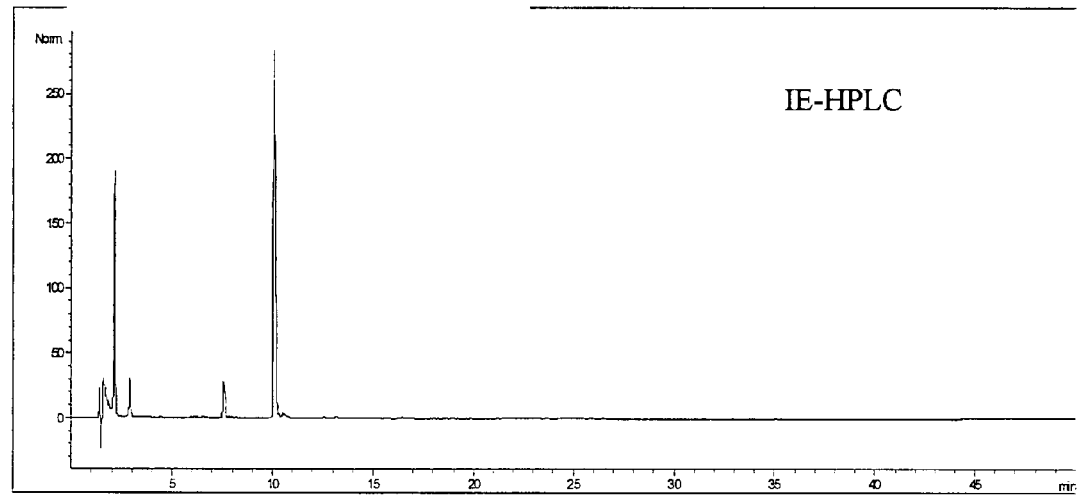
Figure 4:
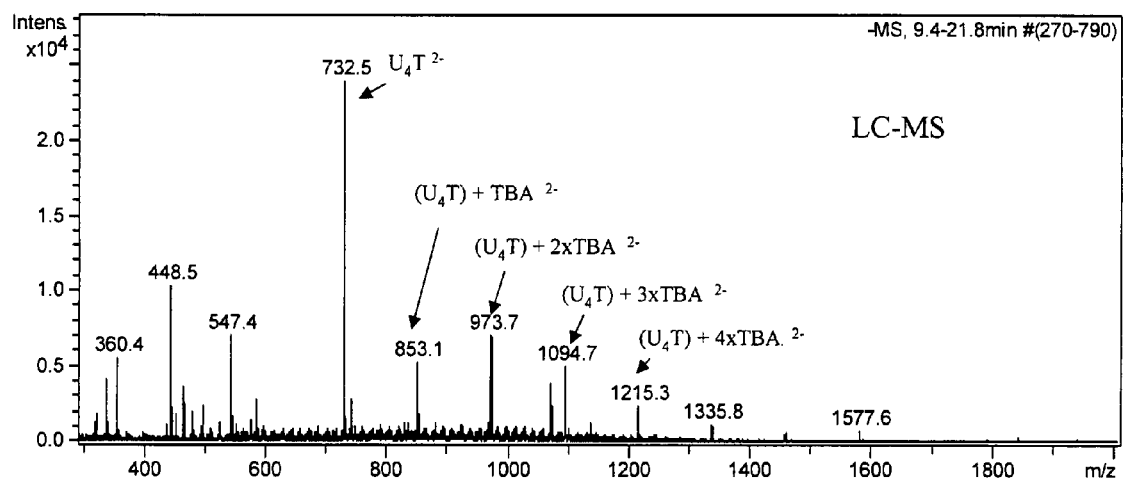

The syntheses was performed on a 1 mmole scale using T-Q-CPG columns from Glen Research, and standard 1 mmole RNA synthesis cycle (10 minute coupling time, 0.45M Tetrazole as an activator). After completion of all synthesis steps, the product mixture (still attached to solid support) was treated with 1M solution of disodium 2-carbamoyl-2-cyanoethylene-1,1-dithiolate in DMF (1 mL, 30 min), washed with water, and then with acetonitrile, and dried on vacuum pump. A solution of $ZnBr_2$ in $CHCl_3$/MeOH (2 mL) was applied into the column with crude oligomer (0.2 mmole) using double-syringe technique, and left at room temperature for 1-6 hours. Solid support with oligomer still attached was washed with a mixture of $CHCl_3$/MeOH (2×10 mL), and then with $CHCl_3$ (10 mL), and dried on vacuum pump for 2 hours. CPG was transferred into the glass bottle and treated with 1M TBAF in THF (200 mL, room temperature, 6 hours). Crude reaction mixture was desalted on PolyPak cartridge using standard procedure, concentrated in vacuo, redissolved in water (200 mL), and analyzed by IE-HPLC and LC-MS. Results are provided in FIGS. 1 to 4.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A nucleoside monomer comprising a 2' silyl containing thiocarbonate protecting group.

2. The nucleoside monomer according to claim 1, wherein said nucleoside monomer has the structure:

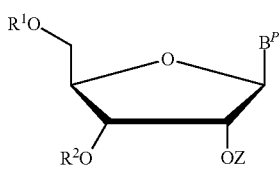
(I)

wherein:
B$^P$ is a protected or unprotected nitrogen-containing base;
R$^1$ and R$^2$ are each independently a phosphoramidite group, a hydroxyl protecting group, or R$^1$ and R$^2$ are linked to form a Markewicz protecting group; and
Z is a silyl containing thiocarbonate protecting group.

3. The nucleoside monomer according to claim 2, wherein Z has the structure:

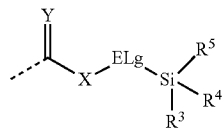
(II)

wherein:
X and Y are each independently a sulfur or oxygen atom;
R$^3$, R$^4$, and R$^5$ are each independently selected from a hydrocarbyl, a substituted hydrocarbyl, an aryl, and a substituted aryl; and
ELg is selected from the group consisting of an ethylene group, a substituted ethylene group, —(CH$_2$CH$_2$O)$_n$—CH$_2$CH$_2$—, substituted —(CH$_2$CH$_2$O)$_n$—CH$_2$CH$_2$—, the following functional groups, and any repeats and combinations of said functional groups:

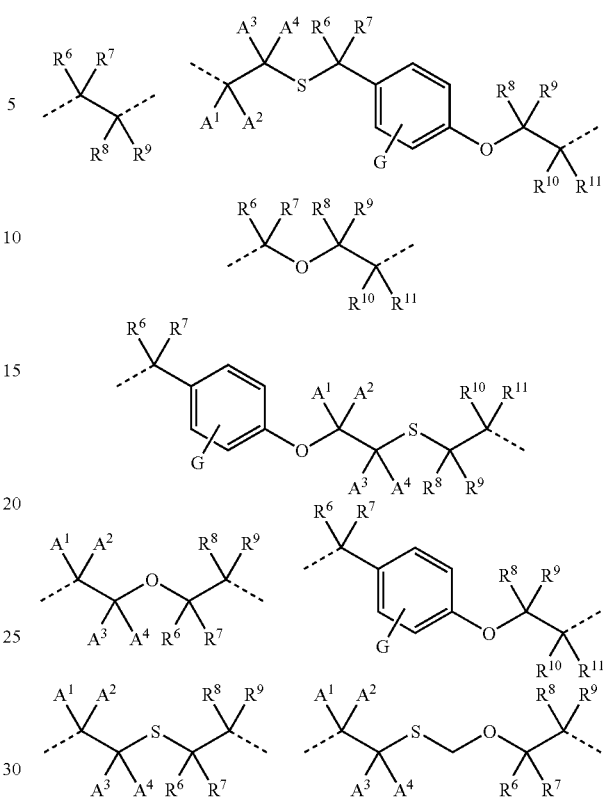

wherein:
each of R$^6$, R$^7$, R$^8$, R$^9$, R$^{10}$, and R$^{11}$ is independently selected from the group consisting of H, a hydrocarbyl, a substituted hydrocarbyl, an aryl, and a substituted aryl;
each of A$^1$, A$^2$, A$^3$, and A$^4$ is independently selected from the group consisting of H and a hydrocarbyl;
G is one or multiple substituents on the phenyl ring independently selected from the group consisting of H, a hydrocarbyl, a substituted hydrocarbyl, an aryl and a substituted aryl; and
n is an integer from 1 to 8.

4. The nucleoside monomer according to claim 3, wherein said nucleoside monomer has the structure of Formula (IIIa);

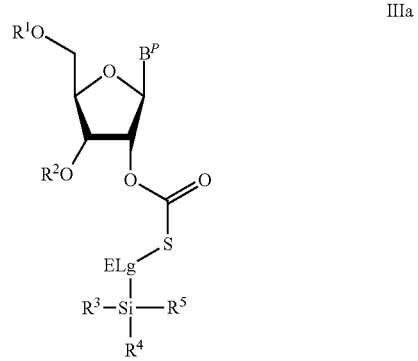
IIIa wherein:
R$^3$, R$^4$ and R$^5$ are each independently selected from a lower alkyl and a lower aryl; and
R$^6$, R$^7$, R$^8$, R$^9$, R$^{10}$, R$^{11}$, A$^1$, A$^2$, A$^3$ and A$^4$ are each independently selected from H and a lower alkyl;

G is H; and n is 1.

5. The nucleoside monomer according to claim 3, wherein said nucleoside monomer has the structure of Formula (IIIb);

[Structure IIIb]

wherein:

$R^3$, $R^4$ and $R^5$ are each independently selected from a lower alkyl and a lower aryl; and $R^6$, $R^7$, $R^8$, $R^9$, $R^{10}$, $R^{11}$, $A^1$, $A^2$, $A^3$ and $A^4$ are each independently H or a lower alkyl;

G is H; and n is 1.

6. The nucleoside monomer according to claim 3, wherein $B^P$ is protected by a silyl containing thiocarbonate protecting group.

7. A method of synthesizing a 2' protected nucleoside monomer, said method comprising:

contacting a nucleoside monomer having the structure:

[Structure IV]

wherein:

$B^P$ is a protected or unprotected nitrogen-containing base; and $R^1$ and $R^2$ are each independently a hydroxyl protecting group, or $R^1$ and $R^2$ are linked to form a Markewicz protecting group;

with a compound having the structure: Z-LG, wherein:

Z is a silyl containing thiocarbonate protecting group; and

LG is a leaving group;

under conditions sufficient to produce a 2' protected nucleoside monomer of the structure of Formula (I)

[Structure I]

wherein $R^1$ and $R^2$ are each independently a hydroxyl protecting group, or $R^1$ and $R^2$ are linked to form a Markewicz protecting group.

8. The method according to claim 7, wherein Z has the structure:

[Structure II]

wherein:

X and Y are each independently a sulfur or oxygen atom;

$R^3$, $R^4$, and $R^5$ are each independently selected from the group consisting of a hydrocarbyl, a substituted hydrocarbyl, an aryl and a substituted aryl; and ELg is selected from the group consisting of an ethylene group, a substituted ethylene group, —(CH$_2$CH$_2$O)$_n$—CH$_2$CH$_2$—, substituted —(CH$_2$CH$_2$O)$_n$—CH$_2$CH$_2$—, the following functional groups, and any repeats and combinations of said functional groups:

[Structures of functional groups]

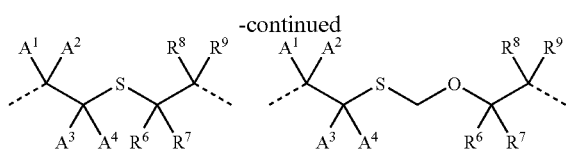

wherein:
each of $R^6$, $R^7$, $R^8$, $R^9$, $R^{10}$, and $R^{11}$ is independently selected from the group consisting of H, a hydrocarbyl, a substituted hydrocarbyl, an aryl and a substituted aryl;
each of $A^1$, $A^2$, $A^3$, and $A^4$ is independently selected from the group consisting of H and a hydrocarbyl;
G is one or multiple substituents on the phenyl ring independently selected from the group consisting of H, a hydrocarbyl, a substituted hydrocarbyl, an aryl and a substituted aryl; and
n is an integer from 1 to 8.

9. The method according to claim 8, wherein $R^1$ and $R^2$ are linked to form a Markewicz protecting group.

10. The method according to claim 9, wherein said Markewicz protecting group is a 1,3-tetraisopropyldisiloxane (TIPS) group.

11. The method according to claim 10, wherein said method further comprises removing said Markewicz protecting group.

12. A nucleic acid comprising the structure:

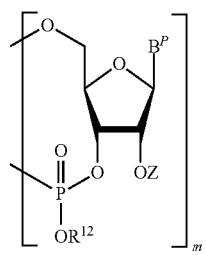

VI wherein:
$B^P$ is a protected or unprotected nitrogen-containing base;
Z is a silyl containing thiocarbonate protecting group;
$R^{12}$ is selected from the group consisting of hydrogen, a hydrocarbyl, a substituted hydrocarbyl, an aryl and a substituted aryl; and
m is an integer greater than 1.

13. The nucleic acid according to claim 12, wherein Z has the structure:

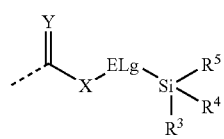

(II)

wherein:
X and Y are each independently a sulfur or oxygen atom;
$R^3$, $R^4$, and $R^5$ are each independently a hydrocarbyl, a substituted hydrocarbyl, an aryl and a substituted aryl; and
ELg is selected from the group consisting of an ethylene group, a substituted ethylene group, —(CH$_2$CH$_2$O)$_n$— CH$_2$CH$_2$—, substituted —(CH$_2$CH$_2$O)$_n$—CH$_2$CH$_2$—, the following functional groups, and any repeats and combinations of said functional groups:

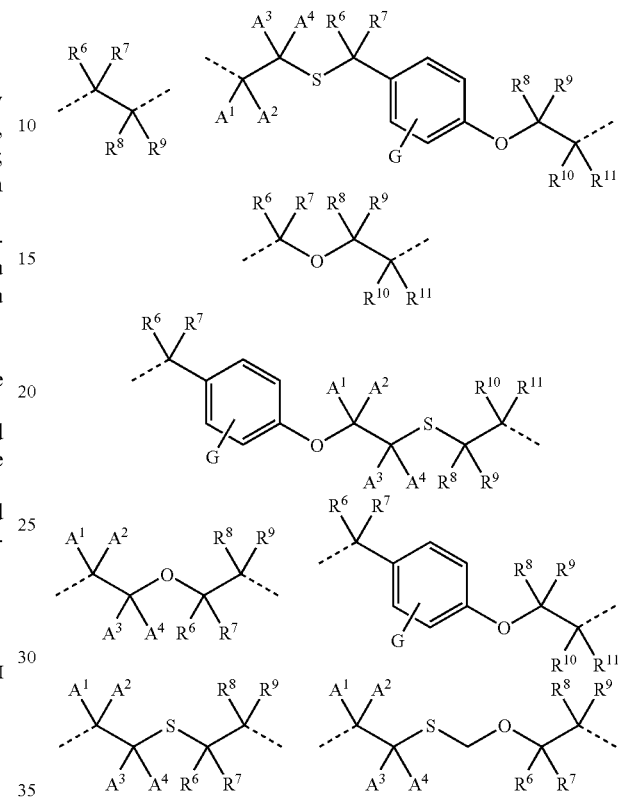

wherein:
each of $R^6$, $R^7$, $R^8$, $R^9$, $R^{10}$, and $R^{11}$ is independently selected from the group consisting of H, a hydrocarbyl, a substituted hydrocarbyl, an aryl and a substituted aryl;
each of $A^1$, $A^2$, $A^3$, and $A^4$ is independently selected from the group consisting of H and a hydrocarbyl;
G is one or multiple substituents on the phenyl ring independently selected from the group consisting of H, a hydrocarbyl, a substituted hydrocarbyl, an aryl and a substituted aryl; and
n is an integer from 1 to 8.

14. A method of synthesizing a nucleic acid, comprising:
(a) providing a nucleoside residue having an unprotected hydroxyl group and a 2' protected nucleoside monomer, wherein said 2' protected nucleoside monomer comprises a 2' silyl containing thiocarbonate protecting group; and
(b) contacting said nucleoside residue and said 2' protected nucleoside monomer under conditions sufficient to covalently bond said 2' protected nucleoside monomer to said nucleoside residue to produce said nucleic acid.

15. The method according to claim 14, wherein said method further comprises exposing said nucleic acid to an oxidizing and deprotecting agent.

16. The method according to claim 15, wherein said method further comprises reiterating said contacting step at least once.

17. The method according to claim 16, further comprising removing said 2' silyl containing thiocarbonate protecting group.

18. The method according to claim 14, wherein said nucleoside residue is covalently bonded to a solid support.

19. The method according to claim 18, wherein said method further comprises cleaving said nucleic acid from said solid support to produce a free nucleic acid.

20. The method according to claim 19, wherein said method further comprises combining said free nucleic acid with a pharmaceutically acceptable vehicle.

21. The method according to claim 14, wherein said method further comprises chemically modifying said nucleic acid to produce a modified nucleic acid.

22. The method according to claim 21, wherein said method further comprises combining said modified nucleic acid with a pharmaceutically acceptable vehicle.

* * * * *

UNITED STATES PATENT AND TRADEMARK OFFICE
CERTIFICATE OF CORRECTION

| | | |
|---|---|---|
| PATENT NO. | : 7,999,087 B2 | Page 1 of 1 |
| APPLICATION NO. | : 11/985598 | |
| DATED | : August 16, 2011 | |
| INVENTOR(S) | : Douglas J Dellinger et al. | |

It is certified that error appears in the above-identified patent and that said Letters Patent is hereby corrected as shown below:

On the face page, in field (75), in "Inventors", in column 1, line 2, delete "Agnleska Sierzchala," and insert -- Agnieszka Sierzchala, --, therefor.

In column 41, line 45, in Claim 2, delete "Markewicz" and insert -- Markiewicz --, therefor.

In column 43, lines 8-20, in Claim 5, after " 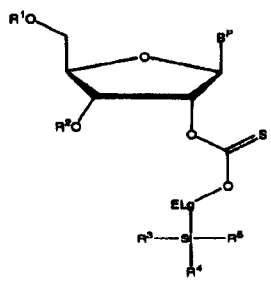 " delete ".".

In column 43, line 57, in Claim 7, delete "Markewicz" and insert -- Markiewicz --, therefor.

In column 44, line 14, in Claim 7, delete "Markewicz" and insert -- Markiewicz --, therefor.

In column 45, line 21, in Claim 9, delete "Markewicz" and insert -- Markiewicz --, therefor.

In column 45, line 23, in Claim 10, delete "Markewicz" and insert -- Markiewicz --, therefor.

In column 45, line 26, in Claim 11, delete "Markewicz" and insert -- Markiewicz --, therefor.

Signed and Sealed this
Third Day of January, 2012

David J. Kappos
*Director of the United States Patent and Trademark Office*